(12) United States Patent
Argento et al.

(10) Patent No.: US 12,403,008 B2
(45) Date of Patent: Sep. 2, 2025

(54) ADJUSTABLE MEDICAL DEVICE

(71) Applicant: SHIFAMED HOLDINGS, LLC, Campbell, CA (US)

(72) Inventors: Claudio Argento, Felton, CA (US); Andrew Backus, Santa Cruz, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 968 days.

(21) Appl. No.: 17/286,724

(22) PCT Filed: Oct. 18, 2019

(86) PCT No.: PCT/US2019/057082
§ 371 (c)(1),
(2) Date: Apr. 19, 2021

(87) PCT Pub. No.: WO2020/082039
PCT Pub. Date: Apr. 23, 2020

(65) Prior Publication Data
US 2021/0378823 A1  Dec. 9, 2021

Related U.S. Application Data

(60) Provisional application No. 62/748,162, filed on Oct. 19, 2018.

(51) Int. Cl.
*A61F 2/24* (2006.01)

(52) U.S. Cl.
CPC .... *A61F 2/2466* (2013.01); *A61F 2220/0008* (2013.01)

(58) Field of Classification Search
CPC .......... A61F 2/2466; A61F 2220/0008; A61F 2/2442; A61F 2250/0029; A61F 2/2454;
(Continued)

(56) References Cited

U.S. PATENT DOCUMENTS

| | | |
|---|---|---|
| 4,725,274 A | 2/1988 | Lane et al. |
| 5,002,563 A | 3/1991 | Pyka et al. |

(Continued)

FOREIGN PATENT DOCUMENTS

| | | |
|---|---|---|
| AU | 2012261727 B2 | 10/2015 |
| AU | 2019246822 B2 | 8/2020 |

(Continued)

OTHER PUBLICATIONS

Argento et al.; U.S. Appl. No. 17/599,710 entitled "Minimal frame prosthetic cardiac valve delivery devices, systems, and methods," filed Sep. 29, 2021.

(Continued)

*Primary Examiner* — Jerrah Edwards
*Assistant Examiner* — Jose H. Trevino, III
(74) *Attorney, Agent, or Firm* — Shay Glenn LLP

(57) ABSTRACT

Medical devices that can be delivered in a first, flexible configuration and subsequently locked into a second, rigid configuration are provided. The device comprises an elongate body having a plurality of slots openings along a bending portion of the body. Using a tension member to shorten the distance between two points along the elongate body causes the device to curve. The device can be locked into the curved configuration.

22 Claims, 10 Drawing Sheets

(58) Field of Classification Search
CPC ... A61F 2230/0091; A61B 2018/00357; A61B 18/1492; A61B 2017/00309; A61B 2017/00867; A61B 2018/00577; A61B 2018/1467; A61B 1/0055; A61B 1/00078; A61B 1/0058; A61B 17/00234; A61B 2017/00314; A61M 2025/09141; A61M 25/09; A61M 25/0138; A61M 25/0147; A61M 25/0043; A61M 25/00; A61M 25/0013; A61M 25/0012; A61M 25/0015; A61M 25/0054; A61M 25/0053; A61M 25/01; A61M 2025/0063; A61M 25/0097; A61M 25/0133; A61M 25/0105; A61M 25/0141; A61M 25/0144

See application file for complete search history.

(56) References Cited

U.S. PATENT DOCUMENTS

| | | |
|---|---|---|
| 5,327,905 A | 7/1994 | Avitall |
| 5,356,424 A | 10/1994 | Buzerak et al. |
| 5,370,685 A | 12/1994 | Stevens |
| 5,582,616 A | 12/1996 | Bolduc et al. |
| 5,716,397 A | 2/1998 | Myers |
| 5,755,601 A | 5/1998 | Jones |
| 5,779,669 A | 7/1998 | Haissaguerre et al. |
| 5,873,835 A | 2/1999 | Hastings et al. |
| 5,944,690 A | 8/1999 | Falwell et al. |
| 5,997,526 A | 12/1999 | Giba et al. |
| 6,048,339 A | 4/2000 | Zirps et al. |
| 6,053,873 A | 4/2000 | Govari et al. |
| 6,254,550 B1 | 7/2001 | McNamara et al. |
| 6,419,695 B1 | 7/2002 | Gabbay |
| 6,419,696 B1 | 7/2002 | Ortiz et al. |
| 6,530,952 B2 | 3/2003 | Vesely |
| 6,533,783 B1 | 3/2003 | Töllner |
| 6,641,553 B1 | 11/2003 | Chee et al. |
| 6,752,813 B2 | 6/2004 | Goldfarb et al. |
| 6,908,478 B2 | 6/2005 | Alferness et al. |
| 6,964,684 B2 | 11/2005 | Ortiz et al. |
| 6,974,476 B2 | 12/2005 | McGuckin, Jr. et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,160,322 B2 | 1/2007 | Gabbay |
| 7,175,656 B2 | 2/2007 | Khairkhahan |
| 7,201,771 B2 | 4/2007 | Lane |
| 7,226,467 B2 | 6/2007 | Lucatero et al. |
| 7,329,279 B2 | 2/2008 | Haug et al. |
| 7,381,219 B2 | 6/2008 | Salahieh et al. |
| 7,445,631 B2 | 11/2008 | Salahieh et al. |
| 7,470,285 B2 | 12/2008 | Nugent et al. |
| 7,527,647 B2 | 5/2009 | Spence |
| 7,534,261 B2 | 5/2009 | Freidman |
| 7,563,267 B2 | 7/2009 | Goldfarb et al. |
| 7,594,903 B2 | 9/2009 | Webler et al. |
| 7,604,646 B2 | 10/2009 | Goldfarb et al. |
| 7,608,091 B2 | 10/2009 | Goldfarb et al. |
| 7,618,449 B2 | 11/2009 | Tremulis et al. |
| 7,621,948 B2 | 11/2009 | Herrmann et al. |
| 7,666,204 B2 | 2/2010 | Thornton et al. |
| 7,704,269 B2 | 4/2010 | St. Goar et al. |
| 7,731,705 B2 | 6/2010 | Wardle |
| 7,748,389 B2 | 7/2010 | Salahich et al. |
| 7,749,266 B2 | 7/2010 | Forster et al. |
| 7,780,725 B2 | 8/2010 | Haug et al. |
| 7,799,069 B2 | 9/2010 | Bailey et al. |
| 7,811,296 B2 | 10/2010 | Goldfarb et al. |
| 7,824,442 B2 | 11/2010 | Salahieh et al. |
| 7,824,443 B2 | 11/2010 | Salahieh et al. |
| 7,846,203 B2 | 12/2010 | Cribier |
| 7,942,927 B2 | 5/2011 | Kaye et al. |
| 7,947,075 B2 | 5/2011 | Goetz et al. |
| 7,951,195 B2 | 5/2011 | Antonsson et al. |
| 7,959,666 B2 | 6/2011 | Salahieh et al. |
| 7,988,724 B2 | 8/2011 | Salahieh et al. |
| 8,021,421 B2 | 9/2011 | Fogarty et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,070,800 B2 | 12/2011 | Lock et al. |
| 8,075,615 B2 | 12/2011 | Eberhardt et al. |
| 8,096,985 B2 | 1/2012 | Legaspi et al. |
| 8,147,541 B2 | 4/2012 | Forster et al. |
| 8,147,542 B2 | 4/2012 | Maisano et al. |
| 8,182,528 B2 | 5/2012 | Salahich et al. |
| 8,216,256 B2 | 7/2012 | Raschdorf et al. |
| 8,236,049 B2 | 8/2012 | Rowe et al. |
| 8,241,351 B2 | 8/2012 | Cabiri |
| 8,251,977 B2 | 8/2012 | Partlett |
| 8,252,050 B2 | 8/2012 | Maisano et al. |
| 8,287,584 B2 | 10/2012 | Salahieh et al. |
| 8,313,526 B2 | 11/2012 | Hoffman et al. |
| 8,323,241 B2 | 12/2012 | Salahleh et al. |
| 8,323,336 B2 | 12/2012 | Hill et al. |
| 8,328,868 B2 | 12/2012 | Paul et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,366,767 B2 | 2/2013 | Zhang |
| 8,403,981 B2 | 3/2013 | Forster et al. |
| 8,403,983 B2 | 3/2013 | Quadri et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,425,593 B2 | 4/2013 | Braido et al. |
| 8,449,599 B2 | 5/2013 | Chau et al. |
| 8,454,686 B2 | 6/2013 | Alkhatib |
| 8,465,541 B2 | 6/2013 | Dwork |
| 8,500,800 B2 | 8/2013 | Maisano et al. |
| 8,512,401 B2 | 8/2013 | Murray et al. |
| 8,523,881 B2 | 9/2013 | Cabiri et al. |
| 8,545,553 B2 | 10/2013 | Zipory et al. |
| 8,556,963 B2 | 10/2013 | Tremulis et al. |
| 8,562,645 B2 | 10/2013 | Stone et al. |
| 8,562,673 B2 | 10/2013 | Yeung et al. |
| 8,579,962 B2 | 11/2013 | Salahieh et al. |
| 8,603,157 B2 | 12/2013 | Seguin et al. |
| 8,603,160 B2 | 12/2013 | Salahleh et al. |
| 8,623,075 B2 | 1/2014 | Murray et al. |
| 8,628,570 B2 | 1/2014 | Seguin |
| 8,641,727 B2 | 2/2014 | Starksen et al. |
| 8,652,202 B2 | 2/2014 | Alon et al. |
| 8,652,203 B2 | 2/2014 | Quadri et al. |
| 8,657,872 B2 | 2/2014 | Seguin |
| 8,685,086 B2 | 4/2014 | Navia et al. |
| 8,696,693 B2 | 4/2014 | Najafi et al. |
| 8,715,300 B2 | 5/2014 | Najafi et al. |
| 8,715,342 B2 | 5/2014 | Zipory et al. |
| 8,740,976 B2 | 6/2014 | Tran et al. |
| 8,784,479 B2 | 7/2014 | Antonsson et al. |
| 8,790,367 B2 | 7/2014 | Nguyen et al. |
| 8,808,368 B2 | 8/2014 | Maisano et al. |
| 8,828,078 B2 | 9/2014 | Salahieh et al. |
| 8,834,564 B2 | 9/2014 | Tuval et al. |
| 8,840,663 B2 | 9/2014 | Salahieh et al. |
| 8,840,664 B2 | 9/2014 | Karapetian et al. |
| 8,845,588 B2 | 9/2014 | Bruszewski |
| 8,852,271 B2 | 10/2014 | Murray et al. |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,900,294 B2 | 12/2014 | Paniagua et al. |
| 8,911,494 B2 | 12/2014 | Hammer et al. |
| 8,920,369 B2 | 12/2014 | Salahieh et al. |
| 8,926,690 B2 | 1/2015 | Kowalsky |
| 8,926,696 B2 | 1/2015 | Cabiri et al. |
| 8,926,697 B2 | 1/2015 | Gross et al. |
| 8,940,002 B2 | 1/2015 | Goertzen |
| 8,940,044 B2 | 1/2015 | Hammer et al. |
| 8,951,299 B2 | 2/2015 | Paul et al. |
| 8,986,371 B2 | 3/2015 | Quill et al. |
| 8,998,980 B2 | 4/2015 | Shipley et al. |
| 9,005,273 B2 | 4/2015 | Salahieh et al. |

(56) References Cited

U.S. PATENT DOCUMENTS

| | | |
|---|---|---|
| 9,011,515 B2 | 4/2015 | Schweich et al. |
| 9,011,523 B2 | 4/2015 | Seguin |
| 9,011,530 B2 | 4/2015 | Reich et al. |
| 9,017,408 B2 | 4/2015 | Siegal et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,056,009 B2 | 6/2015 | Keränen |
| 9,061,120 B2 | 6/2015 | Osypka et al. |
| 9,078,747 B2 | 7/2015 | Conklin |
| 9,095,431 B2 | 8/2015 | Yu et al. |
| 9,119,719 B2 | 9/2015 | Zipory et al. |
| 9,125,739 B2 | 9/2015 | Paniagua et al. |
| 9,125,740 B2 | 9/2015 | Morriss et al. |
| 9,155,619 B2 | 10/2015 | Liu et al. |
| 9,168,129 B2 | 10/2015 | Valdez et al. |
| 9,168,131 B2 | 10/2015 | Yohanan et al. |
| 9,173,713 B2 | 11/2015 | Hart et al. |
| 9,173,737 B2 | 11/2015 | Hill et al. |
| 9,180,006 B2 | 11/2015 | Keränen |
| 9,226,823 B2 | 1/2016 | Dwork |
| 9,232,995 B2 | 1/2016 | Kovalsky et al. |
| 9,277,994 B2 | 3/2016 | Miller et al. |
| 9,289,297 B2 | 3/2016 | Wilson et al. |
| 9,295,547 B2 | 3/2016 | Costello et al. |
| 9,301,756 B2 | 4/2016 | Wardle |
| 9,301,836 B2 | 4/2016 | Buchbinder et al. |
| 9,320,597 B2 | 4/2016 | Savage et al. |
| 9,343,224 B2 | 5/2016 | Zilbershlag |
| 9,358,110 B2 | 6/2016 | Paul et al. |
| 9,414,915 B2 | 8/2016 | Lombardi et al. |
| 9,427,315 B2 | 8/2016 | Schweich et al. |
| 9,439,757 B2 | 9/2016 | Wallace et al. |
| 9,468,525 B2 | 10/2016 | Kovalsky |
| 9,474,606 B2 | 10/2016 | Zipory et al. |
| 9,474,840 B2 | 10/2016 | Siess |
| 9,480,559 B2 | 11/2016 | Vidlund et al. |
| 9,492,273 B2 | 11/2016 | Wallace et al. |
| 9,526,487 B2 | 12/2016 | Rahmani |
| 9,526,609 B2 | 12/2016 | Salahieh et al. |
| 9,532,868 B2 | 1/2017 | Braido |
| 9,532,870 B2 | 1/2017 | Cooper et al. |
| 9,561,102 B2 | 2/2017 | Rust et al. |
| 9,579,198 B2 | 2/2017 | Deem et al. |
| 9,636,224 B2 | 5/2017 | Zipory et al. |
| 9,636,481 B2 | 5/2017 | Campbell et al. |
| 9,662,202 B2 | 5/2017 | Quill et al. |
| 9,662,206 B2 | 5/2017 | Börtlein et al. |
| 9,662,209 B2 | 5/2017 | Gross et al. |
| 9,675,454 B2 | 6/2017 | Vidlund et al. |
| 9,681,952 B2 | 6/2017 | Hacohen et al. |
| 9,687,343 B2 | 6/2017 | Börtlein et al. |
| 9,724,192 B2 | 8/2017 | Sheps et al. |
| 9,730,790 B2 | 8/2017 | Quadri et al. |
| 9,730,793 B2 | 8/2017 | Reich et al. |
| 9,744,031 B2 | 8/2017 | Girard et al. |
| 9,744,038 B2 | 8/2017 | Dahlgren et al. |
| 9,750,605 B2 | 9/2017 | Ganesan et al. |
| 9,763,779 B2 | 9/2017 | Börtlein et al. |
| 9,763,780 B2 | 9/2017 | Morriss et al. |
| 9,814,611 B2 | 11/2017 | Cartledge et al. |
| 9,827,090 B2 | 11/2017 | Hill et al. |
| 9,861,480 B2 | 1/2018 | Zakai et al. |
| 9,867,700 B2 | 1/2018 | Bakis et al. |
| 9,867,702 B2 | 1/2018 | Keränen et al. |
| 9,877,833 B1 | 1/2018 | Bishop et al. |
| 9,883,941 B2 | 2/2018 | Hastings et al. |
| 9,889,003 B2 | 2/2018 | Börtlein et al. |
| 9,895,221 B2 | 2/2018 | Vidlund |
| 9,895,222 B2 | 2/2018 | Zeng et al. |
| 9,901,444 B2 | 2/2018 | Valdez et al. |
| 9,918,840 B2 | 3/2018 | Reich et al. |
| D815,744 S | 4/2018 | Ratz et al. |
| 9,949,825 B2 | 4/2018 | Braido et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,647 B2 | 5/2018 | Ganesan et al. |
| 9,974,650 B2 | 5/2018 | Nguyen-Thien-Nhon et al. |
| 9,999,502 B2 | 6/2018 | Nasr et al. |
| 9,999,504 B2 | 6/2018 | Czyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,832 B2 | 7/2018 | Quill et al. |
| 10,029,037 B2 | 7/2018 | Muller et al. |
| 10,034,747 B2 | 7/2018 | Harewood |
| 10,034,749 B2 | 7/2018 | Spence et al. |
| 10,039,637 B2 | 8/2018 | Maimon et al. |
| 10,045,846 B2 | 8/2018 | Bonyuet et al. |
| 10,052,198 B2 | 8/2018 | Chau et al. |
| 10,052,199 B2 | 8/2018 | Spence et al. |
| 10,058,318 B2 | 8/2018 | Tegzes |
| 10,058,321 B2 | 8/2018 | Sampson et al. |
| 10,058,424 B2 | 8/2018 | Cooper et al. |
| 10,064,719 B2 | 9/2018 | Börtlein et al. |
| 10,070,954 B2 | 9/2018 | Braido et al. |
| 10,092,400 B2 | 10/2018 | Jimenez et al. |
| 10,098,734 B2 | 10/2018 | Hoang |
| 10,105,217 B2 | 10/2018 | Keränen |
| 10,105,224 B2 | 10/2018 | Buchbinder et al. |
| 10,117,744 B2 | 11/2018 | Ratz et al. |
| 10,130,464 B2 | 11/2018 | Meiri et al. |
| 10,130,471 B2 | 11/2018 | Keränen et al. |
| 10,143,552 B2 | 12/2018 | Wallace et al. |
| 10,149,759 B2 | 12/2018 | Naor |
| 10,172,708 B2 | 1/2019 | Anderson |
| 10,172,711 B2 | 1/2019 | Keränen |
| 10,179,042 B2 | 1/2019 | Braido et al. |
| 10,188,514 B2 | 1/2019 | Nasr |
| 10,195,021 B2 | 2/2019 | Keränen et al. |
| 10,195,025 B2 | 2/2019 | Levi et al. |
| 10,195,027 B2 | 2/2019 | Nasr |
| 10,195,028 B2 | 2/2019 | Hosmer et al. |
| 10,195,029 B2 | 2/2019 | Keränen |
| 10,201,418 B2 | 2/2019 | Biadillah et al. |
| 10,206,775 B2 | 2/2019 | Kovalsky et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,226,339 B2 | 3/2019 | Spence et al. |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,314,701 B2 | 6/2019 | Von Segesser et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,338,724 B2 | 7/2019 | Zhao |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,130 B2 | 7/2019 | Armer et al. |
| 10,363,131 B2 | 7/2019 | Eidenschink et al. |
| 10,368,986 B2 | 8/2019 | Gosal et al. |
| 10,368,990 B2 | 8/2019 | Noe et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,426,608 B2 | 10/2019 | Salahieh et al. |
| 10,433,961 B2 | 10/2019 | McLean |
| 10,470,881 B2 | 11/2019 | Noe et al. |
| 10,478,291 B2 | 11/2019 | Nguyen et al. |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |

(56) References Cited

U.S. PATENT DOCUMENTS

| | | |
|---|---|---|
| 10,524,901 B2 | 1/2020 | Quadri et al. |
| 10,548,729 B2 | 2/2020 | Zipory et al. |
| 10,568,737 B2 | 2/2020 | Noe et al. |
| 10,575,951 B2 | 3/2020 | Johnson et al. |
| 10,603,165 B2 | 3/2020 | Maimon et al. |
| 10,639,143 B2 | 5/2020 | Oba |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,709,552 B2 | 7/2020 | Backus et al. |
| 10,716,662 B2 | 7/2020 | Delaloye et al. |
| 10,722,351 B2 | 7/2020 | Griffin et al. |
| 10,722,352 B2 | 7/2020 | Spence |
| 10,722,353 B2 | 7/2020 | Levi |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,888,421 B2 | 1/2021 | Hariton et al. |
| 10,912,644 B2 | 2/2021 | Argento et al. |
| 10,973,629 B2 | 4/2021 | Levi et al. |
| 10,973,630 B2 | 4/2021 | Torrianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,103,345 B2 | 8/2021 | Levi et al. |
| 11,147,670 B2 | 10/2021 | Hayoz et al. |
| 11,234,818 B2 | 2/2022 | Zerkowski et al. |
| 11,547,563 B2 | 1/2023 | Keränen et al. |
| 2002/0173841 A1 | 11/2002 | Ortiz et al. |
| 2003/0114913 A1 | 6/2003 | Spenser et al. |
| 2003/0233142 A1 | 12/2003 | Morales et al. |
| 2004/0039442 A1 | 2/2004 | St. Goar et al. |
| 2004/0044350 A1 | 3/2004 | Martin et al. |
| 2005/0137686 A1 | 6/2005 | Salahleh et al. |
| 2005/0137687 A1 | 6/2005 | Salahleh et al. |
| 2005/0137691 A1 | 6/2005 | Salahleh et al. |
| 2005/0137694 A1 | 6/2005 | Haug et al. |
| 2005/0137696 A1 | 6/2005 | Salahieh et al. |
| 2005/0165344 A1 | 7/2005 | Dobak, III |
| 2005/0240202 A1 | 10/2005 | Shennib et al. |
| 2005/0277839 A1 | 12/2005 | Alderman et al. |
| 2006/0009841 A1 | 1/2006 | McGuckin, Jr. et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0195134 A1 | 8/2006 | Crittenden |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0027533 A1 | 2/2007 | Douk |
| 2007/0038292 A1 | 2/2007 | Danielpour |
| 2007/0051377 A1* | 3/2007 | Douk .................. A61B 17/0401 128/897 |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0275503 A1 | 11/2008 | Spence et al. |
| 2008/0275540 A1 | 11/2008 | Wen |
| 2009/0030504 A1 | 1/2009 | Weber et al. |
| 2009/0088836 A1 | 4/2009 | Bishop et al. |
| 2009/0093826 A1 | 4/2009 | Warder-Gabaldon |
| 2009/0138079 A1 | 5/2009 | Tuval et al. |
| 2009/0157174 A1 | 6/2009 | Yoganathan et al. |
| 2009/0192601 A1 | 7/2009 | Rafiee et al. |
| 2009/0209950 A1 | 8/2009 | Starksen |
| 2009/0222026 A1 | 9/2009 | Rothstein et al. |
| 2009/0276040 A1 | 11/2009 | Rowe et al. |
| 2009/0299471 A1 | 12/2009 | Keranen |
| 2010/0010520 A1 | 1/2010 | Takahashi et al. |
| 2010/0049239 A1 | 2/2010 | McGuckin, Jr. et al. |
| 2010/0076497 A1 | 3/2010 | Zwirkoski |
| 2010/0076549 A1 | 3/2010 | Keidar et al. |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1 | 12/2010 | Navia et al. |
| 2011/0022164 A1 | 1/2011 | Quinn et al. |
| 2011/0040366 A1 | 2/2011 | Goetz et al. |
| 2011/0046600 A1 | 2/2011 | Crank |
| 2011/0208298 A1 | 8/2011 | Tuval |
| 2011/0224785 A1 | 9/2011 | Hacohen |
| 2011/0245911 A1 | 10/2011 | Quill et al. |
| 2011/0288637 A1 | 11/2011 | De Marchena |
| 2011/0313515 A1 | 12/2011 | Quadri et al. |
| 2011/0319989 A1 | 12/2011 | Lane et al. |
| 2012/0022633 A1 | 1/2012 | Olson et al. |
| 2012/0053680 A1 | 3/2012 | Bolling et al. |
| 2012/0053682 A1 | 3/2012 | Kovalsky et al. |
| 2012/0101572 A1 | 4/2012 | Kovalsky et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277734 A1 | 11/2012 | Geotz et al. |
| 2012/0277853 A1 | 11/2012 | Rothstein |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0116779 A1 | 5/2013 | Weber |
| 2013/0123912 A1 | 5/2013 | Tung et al. |
| 2013/0172992 A1 | 7/2013 | Gross et al. |
| 2013/0253643 A1 | 9/2013 | Rolando et al. |
| 2013/0274873 A1 | 10/2013 | Delaloye et al. |
| 2013/0282113 A1 | 10/2013 | Punga et al. |
| 2013/0325110 A1 | 12/2013 | Khalil et al. |
| 2013/0331931 A1 | 12/2013 | Gregg et al. |
| 2014/0005768 A1 | 1/2014 | Thomas et al. |
| 2014/0031928 A1 | 1/2014 | Murphy et al. |
| 2014/0081154 A1 | 3/2014 | Toth |
| 2014/0194983 A1 | 7/2014 | Kovalsky et al. |
| 2014/0200649 A1 | 7/2014 | Essinger et al. |
| 2014/0222136 A1 | 8/2014 | Geist et al. |
| 2014/0228943 A1 | 8/2014 | Stigall et al. |
| 2014/0249621 A1 | 9/2014 | Eldenschink |
| 2014/0257467 A1 | 9/2014 | Lane et al. |
| 2014/0277382 A1 | 9/2014 | Dolan et al. |
| 2014/0277409 A1 | 9/2014 | Börtlein et al. |
| 2014/0277427 A1 | 9/2014 | Ratz et al. |
| 2014/0296966 A1 | 10/2014 | Braido et al. |
| 2014/0324163 A1 | 10/2014 | Keränen et al. |
| 2014/0350669 A1 | 11/2014 | Gillespie et al. |
| 2015/0005764 A1 | 1/2015 | Hanson et al. |
| 2015/0005874 A1 | 1/2015 | Vidlund et al. |
| 2015/0018876 A1 | 1/2015 | Ewers et al. |
| 2015/0051709 A1 | 2/2015 | Vasquez et al. |
| 2015/0094802 A1 | 4/2015 | Buchbinder et al. |
| 2015/0134055 A1 | 5/2015 | Spence et al. |
| 2015/0173897 A1 | 6/2015 | Raanani et al. |
| 2015/0250480 A1 | 9/2015 | Featherstone |
| 2015/0265403 A1 | 9/2015 | Keränen |
| 2015/0272737 A1 | 10/2015 | Dale et al. |
| 2015/0297346 A1 | 10/2015 | Duffy et al. |

(56) References Cited

U.S. PATENT DOCUMENTS

| | | |
|---|---|---|
| 2015/0305863 A1 | 10/2015 | Gray et al. |
| 2015/0328000 A1 | 11/2015 | Ratz et al. |
| 2015/0335290 A1 | 11/2015 | Hunter |
| 2015/0335426 A1 | 11/2015 | Lim et al. |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2016/0089126 A1 | 3/2016 | Guo |
| 2016/0095705 A1 | 4/2016 | Keränen et al. |
| 2016/0113764 A1 | 4/2016 | Sheahan et al. |
| 2016/0143689 A1 | 5/2016 | Ditter |
| 2016/0143731 A1 | 5/2016 | Backus et al. |
| 2016/0151153 A1 | 6/2016 | Sandstrom |
| 2016/0166380 A1 | 6/2016 | Seguin et al. |
| 2016/0206853 A1 | 7/2016 | Bolduc et al. |
| 2016/0228247 A1 | 8/2016 | Maimon et al. |
| 2016/0235526 A1 | 8/2016 | Lashinski et al. |
| 2016/0235529 A1 | 8/2016 | Ma et al. |
| 2016/0310268 A1 | 10/2016 | Oba |
| 2016/0324637 A1 | 11/2016 | Hlavka et al. |
| 2016/0324639 A1 | 11/2016 | Nguyen et al. |
| 2016/0331523 A1 | 11/2016 | Chau et al. |
| 2016/0346080 A1 | 12/2016 | Righini et al. |
| 2017/0056163 A1 | 3/2017 | Tayeb et al. |
| 2017/0071732 A1 | 3/2017 | Conklin et al. |
| 2017/0079790 A1 | 3/2017 | Vidlund et al. |
| 2017/0112624 A1 | 4/2017 | Patel |
| 2017/0119524 A1 | 5/2017 | Salahich et al. |
| 2017/0128203 A1 | 5/2017 | Zhang et al. |
| 2017/0156723 A1 | 6/2017 | Keating et al. |
| 2017/0165054 A1 | 6/2017 | Benson et al. |
| 2017/0165057 A9 | 6/2017 | Morriss et al. |
| 2017/0189177 A1 | 7/2017 | Schweich et al. |
| 2017/0216025 A1 | 8/2017 | Nitzan et al. |
| 2017/0245850 A1 | 8/2017 | Call et al. |
| 2017/0258585 A1 | 9/2017 | Marquez et al. |
| 2017/0273788 A1 | 9/2017 | O'Carroll et al. |
| 2017/0273789 A1 | 9/2017 | Yaron et al. |
| 2017/0281341 A1 | 10/2017 | Lim et al. |
| 2017/0311937 A1 | 11/2017 | Bambury et al. |
| 2017/0348099 A1 | 12/2017 | Mendelson et al. |
| 2018/0021546 A1* | 1/2018 | McDermott ...... A61M 25/0147 604/95.04 |
| 2018/0049868 A1 | 2/2018 | Board et al. |
| 2018/0049873 A1 | 2/2018 | Manash et al. |
| 2018/0055628 A1 | 3/2018 | Patel et al. |
| 2018/0092763 A1 | 4/2018 | Dagan et al. |
| 2018/0110622 A1 | 4/2018 | Gregg et al. |
| 2018/0116790 A1 | 5/2018 | Ratz et al. |
| 2018/0125649 A1 | 5/2018 | Nasar |
| 2018/0125651 A1 | 5/2018 | Nasar et al. |
| 2018/0133003 A1 | 5/2018 | Levi |
| 2018/0177592 A1 | 6/2018 | Benichou et al. |
| 2018/0177594 A1* | 6/2018 | Patel ................. A61F 2/2427 |
| 2018/0206982 A1 | 7/2018 | Haivatov et al. |
| 2018/0206986 A1 | 7/2018 | Noe et al. |
| 2018/0206992 A1 | 7/2018 | Brown |
| 2018/0207395 A1 | 7/2018 | Bulman et al. |
| 2018/0214267 A1 | 8/2018 | Lally et al. |
| 2018/0214270 A1 | 8/2018 | Subramanian et al. |
| 2018/0221014 A1 | 8/2018 | Darabian |
| 2018/0228608 A1 | 8/2018 | Sheps et al. |
| 2018/0228610 A1 | 8/2018 | Lashinski et al. |
| 2018/0235443 A1 | 8/2018 | Smith et al. |
| 2018/0250126 A1 | 9/2018 | O'Connor et al. |
| 2018/0250132 A1 | 9/2018 | Ketai et al. |
| 2018/0263764 A1* | 9/2018 | Manash ............. A61F 2/2427 |
| 2018/0280171 A1 | 10/2018 | Gloss et al. |
| 2018/0289473 A1 | 10/2018 | Rajagopal et al. |
| 2018/0289474 A1 | 10/2018 | Rajagopal et al. |
| 2018/0289478 A1 | 10/2018 | Quill |
| 2018/0289480 A1 | 10/2018 | D'ambra et al. |
| 2018/0289485 A1 | 10/2018 | Rajagopal et al. |
| 2018/0296335 A1 | 10/2018 | Miyashiro |
| 2018/0296338 A1 | 10/2018 | Rabito et al. |
| 2018/0318079 A1 | 11/2018 | Patel et al. |
| 2018/0325665 A1 | 11/2018 | Gurovich et al. |
| 2018/0333259 A1 | 11/2018 | Dibie |
| 2018/0344303 A1 | 12/2018 | Bambury et al. |
| 2018/0344454 A1 | 12/2018 | Mauch et al. |
| 2018/0344459 A1 | 12/2018 | Spence et al. |
| 2018/0344971 A1 | 12/2018 | Suzuki et al. |
| 2018/0360600 A1 | 12/2018 | Zhuang et al. |
| 2018/0368830 A1 | 12/2018 | O'Carroll et al. |
| 2019/0000615 A1 | 1/2019 | Tayeb et al. |
| 2019/0000625 A1 | 1/2019 | O'Carroll et al. |
| 2019/0008635 A1 | 1/2019 | Francis et al. |
| 2019/0008639 A1 | 1/2019 | Landon et al. |
| 2019/0008640 A1 | 1/2019 | Cooper et al. |
| 2019/0015205 A1 | 1/2019 | Rajagopal et al. |
| 2019/0021859 A1 | 1/2019 | O'Carrol et al. |
| 2019/0046315 A1 | 2/2019 | Gao et al. |
| 2019/0053894 A1 | 2/2019 | Levi et al. |
| 2019/0053895 A1 | 2/2019 | Levi |
| 2019/0053898 A1 | 2/2019 | Maimon et al. |
| 2019/0053899 A1 | 2/2019 | Levi |
| 2019/0053903 A1 | 2/2019 | Rohl et al. |
| 2019/0060068 A1 | 2/2019 | Cope et al. |
| 2019/0060069 A1 | 2/2019 | Maimon et al. |
| 2019/0060071 A1 | 2/2019 | Lane et al. |
| 2019/0076244 A1 | 3/2019 | Yohanan et al. |
| 2019/0076664 A1 | 3/2019 | Ollivier |
| 2019/0117392 A1 | 4/2019 | Quadri et al. |
| 2019/0133756 A1 | 5/2019 | Zhang et al. |
| 2019/0133757 A1 | 5/2019 | Zhang et al. |
| 2019/0142589 A1 | 5/2019 | Basude |
| 2019/0159770 A1 | 5/2019 | Rohl et al. |
| 2019/0160292 A1 | 5/2019 | Peichel et al. |
| 2019/0167425 A1 | 6/2019 | Reich et al. |
| 2019/0183649 A1 | 6/2019 | Allen et al. |
| 2019/0192288 A1 | 6/2019 | Levi et al. |
| 2019/0192296 A1 | 6/2019 | Schwartz et al. |
| 2019/0201191 A1 | 7/2019 | McLean et al. |
| 2019/0209311 A1 | 7/2019 | Zhang et al. |
| 2019/0209312 A1 | 7/2019 | Zhang et al. |
| 2019/0209313 A1 | 7/2019 | Zhang et al. |
| 2019/0209314 A1 | 7/2019 | Zhang et al. |
| 2019/0209315 A1 | 7/2019 | Zhang et al. |
| 2019/0209316 A1 | 7/2019 | Zhang et al. |
| 2019/0209317 A1 | 7/2019 | Zhang et al. |
| 2019/0209318 A1 | 7/2019 | Zhang et al. |
| 2019/0209320 A1 | 7/2019 | Drasler et al. |
| 2019/0231520 A1 | 8/2019 | Desrosiers et al. |
| 2019/0240023 A1 | 8/2019 | Spence et al. |
| 2019/0246916 A1 | 8/2019 | Kuraguntla et al. |
| 2019/0254816 A1 | 8/2019 | Anderson et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328515 A1 | 10/2019 | Peterson et al. |
| 2019/0328518 A1 | 10/2019 | Neumann |
| 2019/0336282 A1 | 11/2019 | Christianson et al. |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0008936 A1 | 1/2020 | Cheema et al. |
| 2020/0022811 A1 | 1/2020 | Griswold et al. |
| 2020/0054453 A1 | 2/2020 | Zerkowski et al. |
| 2020/0060813 A1 | 2/2020 | Nguyen et al. |
| 2020/0060820 A1 | 2/2020 | Ben-Zvi et al. |
| 2020/0060852 A1 | 2/2020 | Argento et al. |
| 2020/0069415 A1 | 3/2020 | Bialas et al. |
| 2020/0078000 A1 | 3/2020 | Rajagopal et al. |
| 2020/0093601 A1 | 3/2020 | Neustadter |
| 2020/0107932 A1 | 4/2020 | Rabito et al. |
| 2020/0107933 A1 | 4/2020 | Oba |
| 2020/0113586 A1 | 4/2020 | Karasic et al. |
| 2020/0113685 A1 | 4/2020 | Miller et al. |
| 2020/0113696 A1 | 4/2020 | Ekvall et al. |

(56) References Cited

U.S. PATENT DOCUMENTS

| | | |
|---|---|---|
| 2020/0138575 A1 | 5/2020 | Tuval |
| 2020/0139082 A1 | 5/2020 | Matlock |
| 2020/0178977 A1 | 6/2020 | Coleman et al. |
| 2020/0188107 A1 | 6/2020 | Gloss et al. |
| 2020/0205800 A1 | 7/2020 | Gilmore et al. |
| 2020/0205969 A1 | 7/2020 | Hacohen |
| 2020/0205974 A1 | 7/2020 | Zerkowski et al. |
| 2020/0205975 A1 | 7/2020 | Khairkhahan |
| 2020/0205979 A1 | 7/2020 | O'Carroll et al. |
| 2020/0214708 A1 | 7/2020 | Sharma |
| 2020/0229806 A1 | 7/2020 | Goldfarb et al. |
| 2020/0229918 A1 | 7/2020 | Pham et al. |
| 2020/0261220 A1 | 8/2020 | Argento et al. |
| 2020/0275921 A1 | 9/2020 | Gilmore et al. |
| 2020/0276017 A1 | 9/2020 | Subramanian et al. |
| 2020/0297489 A1 | 9/2020 | Bishop et al. |
| 2020/0297491 A1 | 9/2020 | Argento et al. |
| 2020/0306040 A1 | 10/2020 | Fung et al. |
| 2020/0323637 A1 | 10/2020 | Banal et al. |
| 2020/0352705 A1 | 11/2020 | Heneghan et al. |
| 2020/0352706 A1 | 11/2020 | Campbell |
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0154009 A1 | 5/2021 | Argento et al. |
| 2021/0161688 A1 | 6/2021 | Shahriari |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0228343 A1 | 7/2021 | Scheinblum et al. |
| 2021/0315693 A1 | 10/2021 | Tabor et al. |
| 2021/0338419 A1 | 11/2021 | Gifford, III et al. |
| 2021/0386542 A1 | 12/2021 | Schankereli et al. |
| 2022/0387755 A1 | 12/2022 | Higgins |
| 2024/0285396 A1 | 8/2024 | Schwartz et al. |
| 2024/0293217 A1 | 9/2024 | Cartledge et al. |
| 2024/0374378 A1 | 11/2024 | Adamek-Bowers et al. |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2016 |
| CA | 2954826 C | 10/2019 |
| CN | 103764216 A | 4/2014 |
| CN | 103974670 A | 8/2014 |
| CN | 105358098 A | 2/2016 |
| CN | 107690323 A | 2/2018 |
| CN | 111110401 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| DE | 102014102650 A1 | 9/2015 |
| EP | 1105181 B1 | 2/2004 |
| EP | 1432369 B1 | 2/2008 |
| EP | 2374415 A1 | 10/2011 |
| EP | 2907479 A1 | 8/2015 |
| EP | 3037064 A1 | 6/2016 |
| EP | 3158975 A1 | 4/2017 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 3244809 B1 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3441045 B1 | 7/2020 |
| EP | 3672528 A1 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | H08131551 A | 5/1996 |
| JP | 2004154177 A | 6/2004 |
| JP | 2008018139 A | 1/2008 |
| JP | 2011506017 A | 3/2011 |
| JP | 2012531270 A | 12/2012 |
| JP | 2014230797 A | 12/2014 |
| JP | 2018515175 A | 6/2018 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |
| WO | WO2007/007873 A1 | 1/2007 |
| WO | WO2007/081820 A1 | 7/2007 |
| WO | WO2009/079475 A2 | 6/2009 |
| WO | WO2010/141847 A1 | 12/2010 |
| WO | WO2011/025945 A1 | 3/2011 |
| WO | WO2012/087842 A1 | 6/2012 |
| WO | WO2012/145545 A1 | 10/2012 |
| WO | WO2013/059747 A1 | 4/2013 |
| WO | WO2013/190910 A1 | 12/2013 |
| WO | WO2015/127264 A1 | 8/2015 |
| WO | WO2015/153755 A2 | 10/2015 |
| WO | WO2015/173609 A1 | 11/2015 |
| WO | WO2015/195823 A1 | 12/2015 |
| WO | WO2016/052145 A1 | 4/2016 |
| WO | WO2016/117169 A1 | 7/2016 |
| WO | WO2016/183485 A1 | 11/2016 |
| WO | WO2017/121193 A1 | 7/2017 |
| WO | WO2017/151566 A1 | 9/2017 |
| WO | WO2017/214098 A1 | 12/2017 |
| WO | WO2018/025260 A1 | 2/2018 |
| WO | WO2018/039561 A1 | 3/2018 |
| WO | WO2018/039589 A1 | 3/2018 |
| WO | WO2018/112429 A1 | 6/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO2019/010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/086958 A1 | 5/2019 |
| WO | WO2019/102484 A1 | 5/2019 |
| WO | WO2019/116369 A1 | 6/2019 |
| WO | WO2019/118371 A1 | 6/2019 |
| WO | WO2019/135011 A1 | 7/2019 |
| WO | WO2019/135028 A1 | 7/2019 |
| WO | WO2019/144036 A1 | 7/2019 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/123719 A1 | 6/2020 |

(56) References Cited

FOREIGN PATENT DOCUMENTS

| WO | WO2020/157018 A1 | 8/2020 |
|---|---|---|
| WO | WO2020/163112 A1 | 8/2020 |
| WO | WO2020/180485 A1 | 9/2020 |
| WO | WO2020/210685 A8 | 10/2020 |
| WO | WO2020/236830 A1 | 11/2020 |
| WO | WO2020/247907 A1 | 12/2020 |
| WO | WO2021/021482 A1 | 2/2021 |
| WO | WO2021/028867 A1 | 2/2021 |
| WO | WO2021/034497 A1 | 2/2021 |
| WO | WO2022/046678 A1 | 3/2022 |
| WO | WO2022/047095 A1 | 3/2022 |
| WO | WO2022/047160 A1 | 3/2022 |
| WO | WO2022/047274 A1 | 3/2022 |
| WO | WO2022/047393 A8 | 3/2022 |
| WO | WO2022/066713 A1 | 3/2022 |
| WO | WO2022/066720 A1 | 3/2022 |
| WO | WO2024/187023 A2 | 9/2024 |

OTHER PUBLICATIONS

Salahieh et al.; U.S. Appl. No. 17/543,555 entitled "Flared prosthetic cardiac valve delivery devices and systems," filed Dec. 6, 2021.
Yang et al.; U.S. Appl. No. 17/651,040 entitled "Anchor for prosthetic cardiac valve delivery devices and systems".
Salahieh.; U.S. Appl. No. 17/655,978 entitled "Anchor position verification for prosthetic cardiac valve devices," filed Mar. 22, 2022.
Saul; U.S. Appl. No. 17/773,193 entitled "Prosthetic cardiac valve delivery devices, systems, and methods," filed Apr. 29, 2022.
Argento et al.; U.S. Appl. No. 18/185,330 entitled "Prosthetic cardiac valve devices, systems, and methods," filed Mar. 16, 2023.
Adamek-Bowers et al.; U.S. Appl. No. 18/255,763 entitled "Mitral valve implants," filed Jun. 2, 2023.
Schaefer; Large heart valves—small heart valves; ISMAAP; Oct. 19, 2015; 5 pages; retrieved from the internet (https://www.ismaap.org/condition-detail/large-heart-valves-small-heart-valves/) on Mar. 21, 2023.
Argento et al.; U.S. Appl. No. 18/002,219 entitled "Minimal frame prosthetic cardiac valve delivery devices, systems, and methods," filed Dec. 16, 2022.
Adamek-Bowers et al.; U.S. Appl. No. 18/043,458 entitled "Prosthetic valve delivery system," filed Feb. 28, 2023.
Backus et al.; U.S. Appl. No. 18/004,609 entitled "Valve delivery system," filed Jan. 6, 2023.
Mulcahy et al.; U.S. Appl. No. 18/043,480 entitled "Prosthetic cardiac valve delivery devices, systems, and methods," filed Feb. 28, 2023.
Adamek-Bowers et al.; U.S. Appl. No. 18/043,499 entitled "Interface for prosthetic cardiac valve and delivery systems," filed Feb. 28, 2023.
Salahieh et al.; U.S. Appl. No. 18/043,519 entitled "Flared prosthetic cardiac valve delivery devices and systems," filed Feb. 28, 2023.
Scott et al.; U.S. Appl. No. 18/043,526 entitled "Access sheath for prosthetic cardiac valve delivery systems," filed Feb. 28, 2023.
Yang et al.; U.S. Appl. No. 18/043,542 entitled "Anchor for prosthetic cardiac valve devices," filed Feb. 28, 2023.
Argento et al.; U.S. Appl. No. 18/246,307 entitled "Systems, methods, and devices for expandable sensors," filed Mar. 22, 2023.
Argento et al.; U.S. Appl. No. 18/246,311 entitled "Prosthetic cardiac valve sensor devices, systems, and methods with imaging," filed Mar. 22, 2023.
Argento et al.; U.S. Appl. No. 17/931,408 entitled "Prosthetic cardiac valve devices, systems, and methods," filed Sep. 12, 2022.
Argento; U.S. Appl. No. 17/906,216 entitled "Prosthetic cardiac valve devices, systems, and methods," filed Sep. 13, 2022.
Argento et al.; U.S. Appl. No. 17/905,556 entitled "Prosthetic cardiac valve devices, systems, and methods," filed Sep. 2, 2022.
Boyd et al.; U.S. Appl. No. 17/995,776 entitled "Valve delivery system" filed Oct. 7, 2022.
Westaby et al.; Adult human valve dimensions and their surgical significance; The American Journal of Cardiology; 53(4); pp. 552-556; Feb. 1984.
Argento et al.; U.S. Appl. No. 18/494,520 entitled "Prosthetic cardiac valve devices, systems, and methods," filed Oct. 25, 2023.
Mulcahy et al.; U.S. Appl. No. 18/573,816 entitled "Prosthetic cardiac valve delivery devices, systems, and methods," filed Dec. 22, 2023.
Boyd et al.; U.S. Appl. No. 18/688,735 entitled "Guide catheter for prosthetic cardiac valve delivery systems, " filed Mar. 1, 2024.
Adamek-Bowers et al.; U.S. Appl. No. 18/693,856 entitled "Tether delivery of cardiac valve," filed Mar. 20, 2024.
Yang et al.; U.S. Appl. No. 18/700,621 entitled "Cardiac valve prosthesis delivery system and methods of use," filed Apr. 11, 2024.
Argento et al.; U.S. Appl. No. 18/639,743 entitled "Prosthetic cardiac valve devices, systems and methods," filed Apr. 18, 2024.
Boyd et al.; U.S. Appl. No. 18/873,271 entitled "Prosthetic heart valve delivery system and method," filed Dec. 9, 2024.
Masterclass; Knit vs. Woven: Learn How to Identify the Two Fabric Types; Jun. 7, 2021; 13 pages; retrieved from the internet (https://www.masterclass.com/articles/knit-vs-woven-learn-how-to-identify-the-two-fabric-types) on Nov. 15, 2024.

\* cited by examiner

ADJUSTABLE MEDICAL DEVICE

CROSS-REFERENCE

This PCT application claims the benefit of U.S. Provisional Application No. 62/748,162, filed Oct. 19, 2018, entitled "Adjustable Medical Device"; which is incorporated herein by reference for all purposes in its entirety.

The subject matter of this application is related to that of U.S. Provisional Application No. 62/720,853, filed Aug. 21, 2018, entitled "Prosthetic Cardiac Valve Devices, Systems, and Methods"; U.S. patent application Ser. No. 16/546,901, filed Aug. 21, 2019, entitled "Prosthetic Cardiac Valve Devices, Systems, and Methods"; U.S. Provisional Application No. 62/742,043, filed Oct. 5, 2018, entitled "Prosthetic Cardiac Valve Devices, Systems, and Methods"; U.S. Provisional Application No. 62/755,996, filed Nov. 5, 2018, entitled "Prosthetic Cardiac Valve Devices, Systems, and Methods"; U.S. patent application Ser. No. 16/594,946, filed Oct. 7, 2019, entitled "Prosthetic Cardiac Valve Devices, Systems, and Methods"; U.S. Provisional Application No. 62/784,280, filed Dec. 21, 2018, entitled "Prosthetic Cardiac Valve Devices, Systems, and Methods"; U.S. Provisional Application No. 62/813,963, filed Mar. 5, 2019, entitled "Prosthetic Cardiac Valve Devices, Systems, and Methods"; U.S. Provisional Application No. 62/815,791, filed Mar. 8, 2019, entitled "Prosthetic Cardiac Valve Devices, Systems, and Methods"; U.S. Provisional Application No. 62/820,570, filed Mar. 19, 2019, entitled "Prosthetic Cardiac Valve Delivery Devices, Systems, and Methods"; U.S. Provisional Application No. 62/828,835, filed Apr. 3, 2019, entitled "Prosthetic Cardiac Valve Devices, Systems, and Methods"; U.S. Provisional Application No. 62/833,425, filed Apr. 12, 2019, entitled "Minimal Frame Prosthetic Cardiac Valve Delivery Devices, Systems, and Methods"; U.S. Provisional Application No. 62/833,430 filed Apr. 12, 2019, entitled "Prosthetic Cardiac Valve Delivery Devices, Systems, and Methods"; U.S. Provisional Application No. 62/851,245, filed May 22, 2019, entitled "Prosthetic Cardiac Valve Devices, Systems, and Methods"; U.S. Provisional Application No. 62/872,016, filed Jul. 9, 2019, entitled "Prosthetic Cardiac Valve Delivery Devices, Systems, and Methods"; U.S. Provisional Application No. 62/873,454, filed Jul. 12, 2019, entitled "Systems, Methods, and Devices for Expandable Sensors"; U.S. Provisional Application No. 62/879,979, filed Jul. 29, 2019, entitled "Prosthetic Cardiac Valve Devices, Systems, and Methods"; and U.S. Provisional Application No. 62/894,565, filed Aug. 30, 2019, entitled "Prosthetic Cardiac Valve Devices, Systems, and Methods"; which are incorporated herein by reference for all purposes in their entireties.

BACKGROUND

Shape-memory devices are commonly used for minimally-invasive medical procedures due to their ability to return to a desired configuration upon release from a delivery device (in which the shape-memory devices are typically constrained in a narrower profile delivery configuration). However, many shape-memory devices require specialized delivery devices and methods to maintain the devices in a delivery configuration which enables minimally-invasive delivery to a target tissue, which may be less than ideal. Additionally, shape-memory devices may not be sufficiently strong enough to be applied in certain medical procedures which may otherwise be accessible for minimally-invasive techniques.

SUMMARY

It would therefore be desirable to provide a medical device which can be transitioned from a small delivery configuration to a larger delivered configuration minimally requiring specialized delivery devices or methods and/or which may be stronger than some commonly-used shape-memory devices. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure generally relates to medical devices and more particularly to elongate medical devices capable of being transitioned from a smaller profile delivery configuration to larger profile delivered configuration.

In a first aspect, a medical device is provided. The device comprises an elongate body having a first configuration and a second configuration, the second configuration having a different shape from the first configuration; shape changing features on the elongate body configured to allow the elongate body to change shape from the first configuration to the second configuration; and a locking mechanism configured to lock the elongate body in the second configuration.

In another aspect, a medical device is provided. The device comprises an elongate body; a spine portion extending along a sidewall of the elongate body; a plurality of openings extending from the spine portion; a shuttle axially movable along the elongate body; a tension member connecting a connection point positioned distally of the shuttle and the shuttle; a pull member extending proximally from the shuttle; and a locking mechanism configured to hold the shuttle in a proximally pulled position, wherein the medical device comprises a relaxed configuration before the shuttle is pulled proximally and a stiffened configuration after the shuttle is pulled proximally, the stiffened configuration causing the medical device to assume a predetermined, curved configuration, and wherein the plurality of openings is configured to have a first shape in the relaxed configuration and a second shape, different from the first shape in the stiffened configuration.

In some embodiments, a width of the openings changes between the first shape and the second shape. The radius of curvature of the predetermined, curved configuration can be determined by a width of the openings. In some embodiments, the plurality of openings comprises openings of varying size. The spine portion can curve around at least a portion of the elongate body. In some embodiments, the spine portion is arranged in a helical pattern around the elongate body. A pitch or coil angle alpha of the predetermined, curved configuration can be determined by a pitch or coil angle of the spine portion. Alternatively, the spine can be straight and the slots angled relative to the spine. The device can comprise a second connection point proximal to the connection point and a second wire connecting the second connection point to a second shuttle positioned proximally to the second connection point. In some embodiments, the device comprises a plurality of shuttles and a plurality of locking mechanisms. In some embodiments, the locking mechanism comprises a pin attached to the shuttle positioned in and configured to slide along a track extending along a length of the elongate body. The track can twist as it extends proximally, forming a locking area for the pin. In some embodiments, the elongate body further comprises a release window configured to allow disengagement of the pull member from the shuttle. The device can be configured to expose the pull member to the release window when the pin is moved to the locking area. In some embodiments, the locking mechanism comprises a flexible screw positioned proximally to the shuttle, the flexible screw configured to be screwed to the shuttle or a component attached to the shuttle. The flexible screw can be configured to be screwed to a spring attached to the shuttle. In some embodiments, the flexible screw is configured to be screwed to a clip attached to the shuttle. The device can be configured to be delivered by a catheter. In some embodiments, a center portion of the device is configured to allow passage of a guidewire therethrough. The device can comprise a catheter through which the medical device can be inserted. In some embodiments, the device is configured to be connected to an end of a catheter.

In another aspect, a method of deploying a medical device is provided. The method comprises advancing an elongate medical device to a target area in a patient's body, the medical device comprising a plurality of openings extending from a spine portion of a wall of the anchor, the medical device advanced in a first slack configuration; moving the medical device into a stiffened configuration by pulling proximally on a shuttle movable along the medical device, causing a tension member connecting the shuttle to a distal connection point to pull the distal connection point proximally; and locking the medical device in the stiff, activated configuration, the activated configuration comprising a predetermined curved shape.

In some embodiments, the method comprising activating the anchor comprises pulling proximally on a pull member attached to the shuttle while maintaining the position of the proximal end of the anchor. Locking the anchor can comprise moving a pin into a stop position along a track. In some embodiments, locking the anchor comprises screwing a screw to a component attached to the shuttle.

In some embodiments, the target area comprises a native valve in a heart in the patient's body. In some embodiments, the method further comprises advancing the elongate medical device from a first side of the native valve to a second side of the native valve.

In some embodiments, the method further comprises capturing one or more structures on the second side of the native valve with the elongate medical device in the first slack configuration prior to moving the elongate medical device into the stiffened configuration. In some embodiments, the native valve comprises a mitral valve, the first side comprises a left atrium, the second side comprises a left ventricle, and the one or more structures comprise one or more chordae tendineae or native leaflets.

In some embodiments, the method further comprises, after moving the medical device into the stiffened configuration, expanding at least a portion of an expandable valve prosthesis within at least a portion the elongate medical device adjacent the native valve, thereby anchoring the valve prosthesis to the native valve. Expanding the valve prosthesis can capture one or more structures of the native valve between the valve prosthesis and the elongate medical device. In some embodiments, the native valve comprises a mitral valve, the first side comprises a left atrium, the second side comprises a left ventricle, and the one or more structures comprise one or more chordae tendineae or native leaflets.

In another aspect, a method of advancing a medical device to a target area is provided. The method comprises advancing an elongate body towards the target area and out of a distal end of a delivery catheter, the elongate body comprising a first curved shape as the elongate body is advanced towards the target area; locking at least a portion of the elongate body into the first curved shape; moving the elongate body into a second curved shape at or near the target area, the second curved shape different from the first curved shape; and locking the elongate body into the second curved shape. For example, a distal portion of the device can be curved during navigation from a distal end of a delivery catheter to the target area. At or near the target area, a larger or different portion of the device can be locked into a desired final shape. In alternate embodiments, the elongate body is delivered out of the delivery catheter such that it follows the shape of the delivery catheter and then upon delivery to the target area the elongate body is locked into its delivery curved shape.

In another aspect, an anchor for use in transcatheter mitral valve repair is provided. The anchor comprises an elongate body; a spine portion along a sidewall of the elongate body; a plurality of openings extending from the spine portion; a connection point fixed to the elongate body; a shuttle positioned proximally to the connection point and axially movable along the elongate body; a wire connecting the connection point and the shuttle; a pull member extending proximally from the shuttle; and a locking mechanism for holding the shuttle in a proximally pulled position, the proximally pulled position causing the anchor to assume a predetermined, curved configuration.

In some embodiments, the spine portion is arranged to traverse a helical path around the elongate body. In other embodiments the slots are angled relative to the spine. The anchor can comprise a second connection point proximal to the connection point and a second wire connecting the second connection point to a second shuttle positioned proximally to the second connection point.

In another aspect, a method of performing transcatheter mitral valve repair is provided. The method comprises advancing a guidewire or guide catheter through an opening in the atrial septum, across a location near the anteromedial commissure; advancing an elongate anchor comprising a plurality of openings extending from a spine portion of a sidewall of the anchor over the guidewire such that the anchor forms at least one coil around the chordae and one coil in the left atrium, the anchor advanced in a first slack configuration; activating the anchor into a stiffened configuration having a predetermined curved shape by pulling proximally on a shuttle movable along the anchor, causing a wire connecting the shuttle to a distal connection point to pull the distal connection point proximally; and locking the anchor in the stiffened configuration. In some embodiments, the anchor is delivered around the chordae and/or the leaflets. In the stiffened configuration, the anchor can be tightened around the chordae and/or the leaflets.

In another aspect, a device for performing non-occlusive ablation is provided. The device comprises an elongate body; one or more electrodes positioned along the elongate body; a spine portion along a sidewall of the elongate body; a plurality of openings extending from the spine portion; a connection point fixed to the elongate body; a shuttle positioned proximally to the connection point and axially movable along the elongate body; a tension member connecting the connection point and the shuttle; a pull member extending proximally from the shuttle; and a locking mechanism for holding the shuttle in a proximally pulled position, the proximally pulled position causing the device to assume a predetermined, curved configuration.

In another aspect, a method for performing non occlusive ablation is provided. The method comprises advancing an elongate ablation device comprising a plurality of openings extending from a spine portion of a sidewall of the ablation device through the vasculature to a target site to be ablated, the ablation device advanced in a first slack configuration; moving the device into a stiffened configuration having a predetermined, curved shape by pulling proximally on a shuttle movable along the device, causing a wire connecting the shuttle to a distal connection point to pull the distal connection point proximally; and energizing one or more electrodes positioned along the device to ablate tissue near the device. In some embodiments, the spine portion is in the outer most position when the device is in a stiffened configuration. The spine portion can comprise electrodes. In some embodiments, the entire spine portion can comprise a metal and act as the electrode.

In some embodiments, the method comprises locking the device into a stiffened configuration. The method can comprise positioning the device against a tissue site to be ablated. In some embodiments, locking the ablation device causes the one or more electrodes to be in contact with the target site.

INCORPORATION BY REFERENCE

All publications and patent applications mentioned in this specification are incorporated herein by reference in their entirety to the same extent as if each individual publication or patent application was specifically and individually indicated to be incorporated by reference.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Provided herein are embodiments of an adjustable medical device. The device can comprise a slackened configuration and one or more stiffened configurations, the stiffened configurations comprising a predetermined curved shape. The device can be locked into the stiffened configuration(s). For example, in some embodiments, the device is percutaneously advanced to a target area within a patient in a slackened or relaxed configuration. Once the device is deployed to or positioned within a target area, it can be locked into a stiffened configuration comprising a predetermined curved shape. Such a device can be used in a number of different applications, as described below.

Figure 1A:
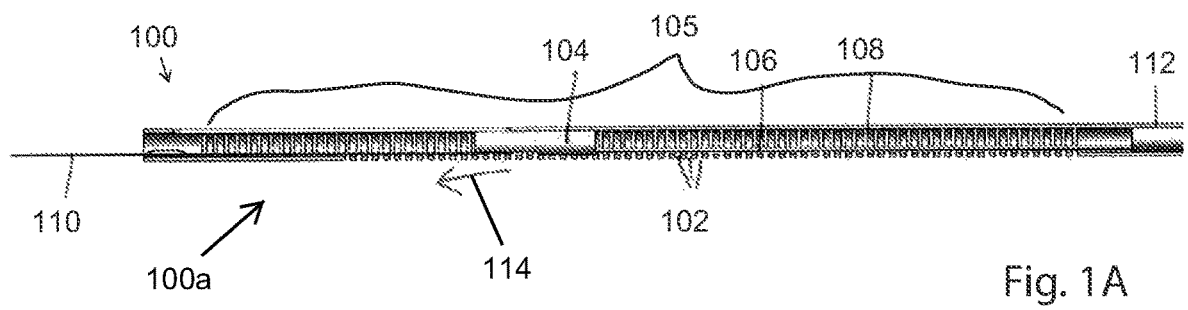
FIGS. 1A and 1B show side and top views, respectively, of an adjustable medical device having undeployed and deployed configurations, according to embodiments of the present disclosure.

FIG. 1A depicts an embodiment of an adjustable medical device 100 in an undeployed, straightened configuration 100a. The device 100 can comprise an elongate body. For example, in some embodiments, the device 100 comprises an elongate, tubular body. The device 100 can be shaped to be delivered percutaneously through or at the end of a catheter. The device 100 comprises a plurality of slots openings 102 surrounding or extending from a spine portion 108. The portion(s) of the device 100 comprising the openings 102 is the collapsing portion(s) 105 of the device 100.

The spine portion 108 of the device may be defined by an area of the bending portion 105 of the device 100 without openings 102. The collapsing of the collapsing portion 105 allows the device 100 to bend at the spine portion 108 of the device 100. In some embodiments, the spine portion 108 can be thin, for example, comprising a width of about 0-10% of a circumference of the elongate body. In other embodiments, the spine portion 108 can be wider, for example, comprising greater than about 10% of a circumference of the elongate body. In some embodiments, the openings 102 surrounding the spine portion 108 are wedged-shaped. Other configurations for the openings are also possible (e.g., slit-shaped, rounded, etc.) as described herein. In some embodiments, the device 100 can be formed from a hyptotube. The openings 102 can be formed by laser cutting, a blade, or the like as will be understood by one of ordinary skill in the art based on the description herein. In some embodiments, the device 100 may comprise a flexible covering or sleeve (e.g., a polymer covering). The cover can help protect surrounding tissue from trauma which may be caused by the openings 102 as the device 100 bends.

The shape or amount of bending of the device 100 in the stiffened configuration 100b is defined by the difference in length between the outer edge of the curve (the spine portion 108) and the inner edge of the curve comprising the openings 102. This difference in length is determined by the width of the openings 102, the sum of which defines the difference in length between the inner and outer edge of the curve.

The device 100 may comprise a plug 112 positioned at a distal portion of the device 100. A tension member 106 (e.g., a wire, an elastic wire, or spring, or the like) may connect the plug 112 and a shuttle 104. The tension member 106 can hold the length of the inner radial surface of the curved portion of the device 100 at its minimal length. It will be appreciated by one of ordinary skill in the art based on the description herein that, in some embodiments, the device 100 may not comprise a plug 112, and the tension member 106 may be connected via another means to another distal point of the device 100. The shuttle 104 is axially movable along a length of the device 100. The shuttle 104 can comprise a cylinder, in some embodiments. Other configurations are also possible (e.g., spherical shape, elliptical shape, rectangular, etc.), as will be understood by one of ordinary skill in the art based on the description herein. The shuttle 104 can be movable within the device 100, over the device 100, or partially within and over the device 100. A pull member 110 (e.g., wire, rod, etc.) may extend proximally from the shuttle 104, and allow the shuttle 104 to be pulled proximally while a proximal end of the device 100 is being held or pushed distally, thereby shortening the distance between the shuttle 104 and the proximal end of the device 100. Alternatively, the proximal end of the device 100 can be pushed distally while the shuttle 104 and/or pull member 110 is held in place. The reduction in distance between the shuttle 104 and the proximal end of the device 100 may define the minimum length of the inner radial surface of the device 100.

Figure 1B:
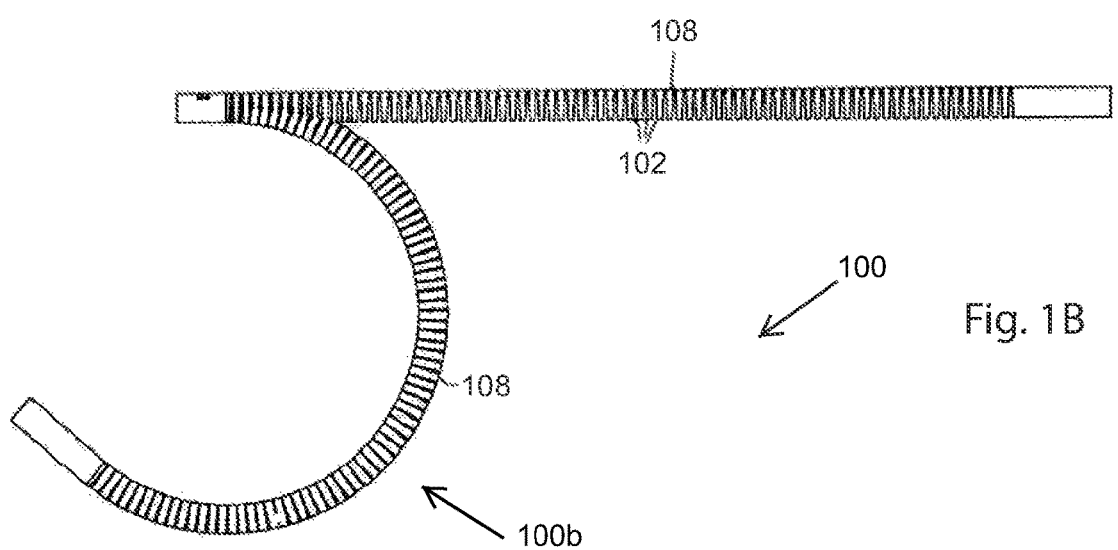

The pull member 110 can be used to pull proximally, in the direction indicated by the arrow 114, on the shuttle 104. The shuttle 104 moving proximally may cause the shape of the openings 102 to change. The width of the openings 102 may decrease as the shuttle 104 moves proximally, thus shortening the side of device 100 positioned away from spine 108. The shortening of one side of the device 100 causes the device 100 to curve away from the spine portion 108, as shown in FIG. 1B.

Figure 1C:
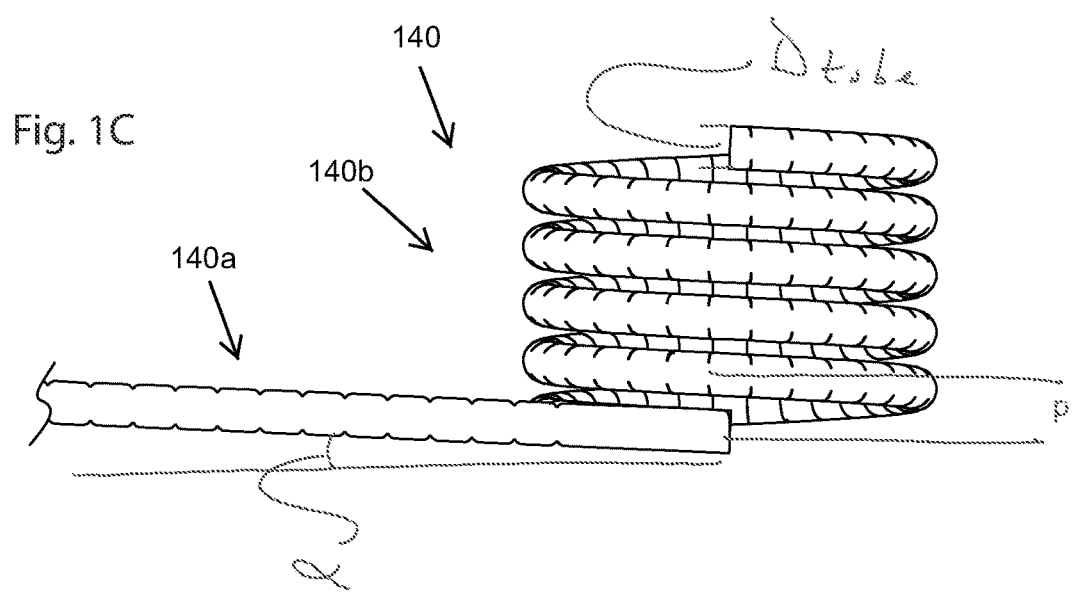
FIGS. 1C, 1D, and 1E show side and perspective views of an adjustable medical device in a relaxed and in a stiffened configuration, according to embodiments of the present disclosure.

In the stiffened configuration 100b, the device 100 can comprise a variety of shapes. For example, the device 100 shown in FIG. 1A may deform into the shape of a portion of a circle as shown in FIG. 1B. In some embodiments, the device 100 comprises a helical shaped device 140 as in FIGS. 1C and 1D in the stiffened configuration 100a, 140a. The helical shape can have a coil angle α, and a pitch p. The coil angle α and coil pitch p of the device 140 in the stiffened configuration 140b can be determined by the angle and pitch of the spine portion 108 of the device 140. The device 140 can comprise any combination of a spiral shape, a conical shape, a frustoconical shape, a helical shape, etc. As shown in the device 140 of FIGS. 1C and 1D, the openings 142 can be arranged at an angle relative to the spine 108 to facilitate helical coiling.

Figure 1D:
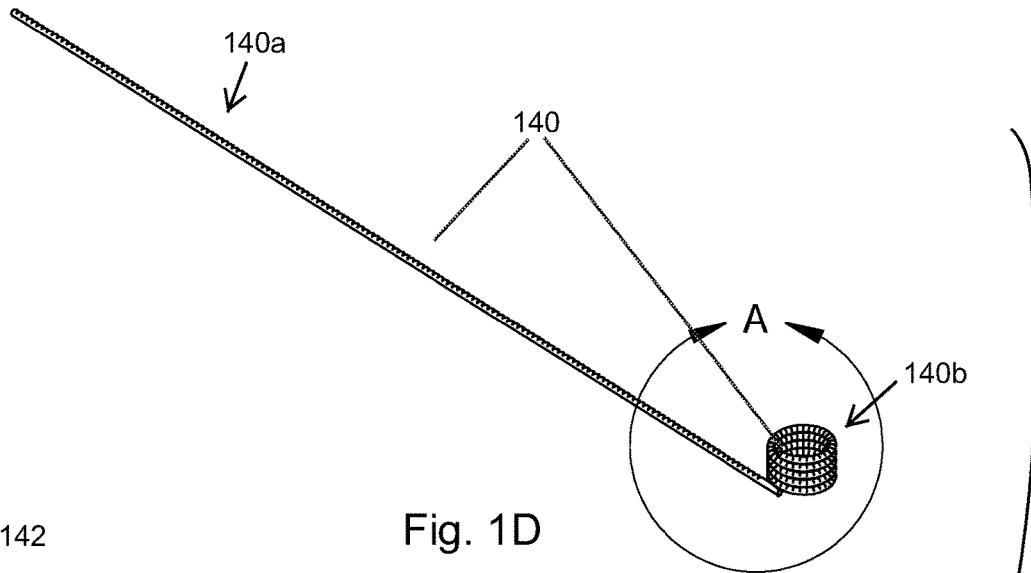
Figure 1E:
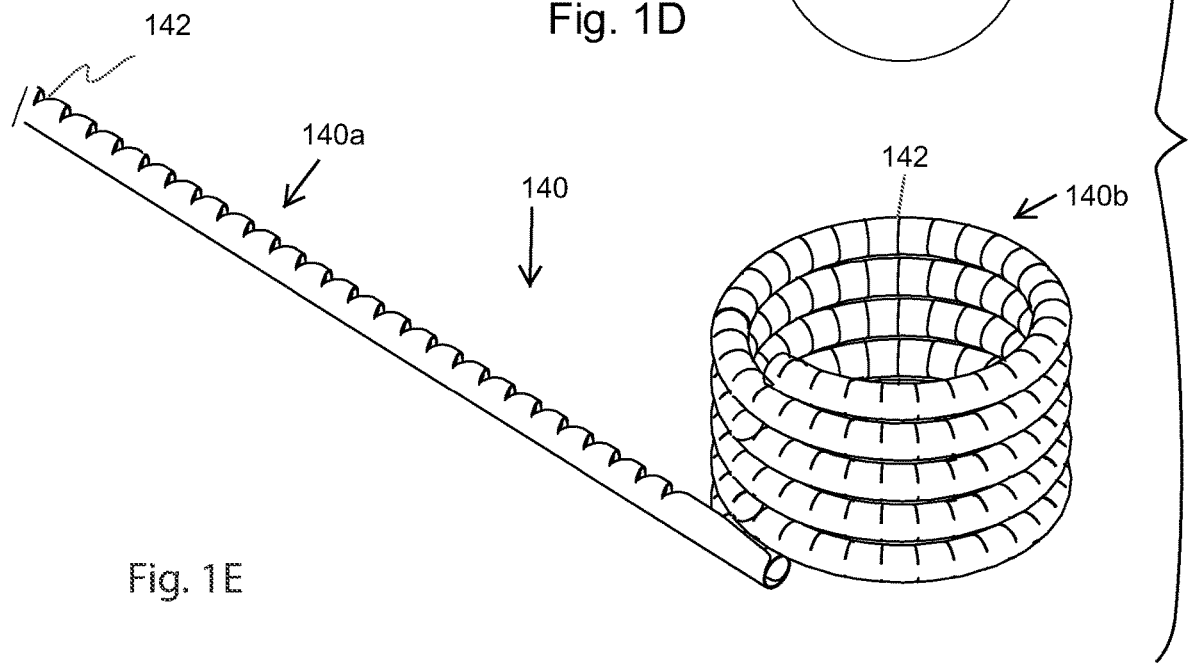

FIG. 1D illustrates a device 140 in a relaxed, straight configuration 140a, and in a stiffened, coiled configuration 140b. FIG. 1E illustrates a magnified view of the portion of FIG. 1D shown in section A. The slots or openings 142 are shown open in the relaxed, straight configuration 140a. In the stiffened, coiled configuration 140b, the slots or openings 142 may be collapsed, allowing the device 100 to curve.

Figure 2A:
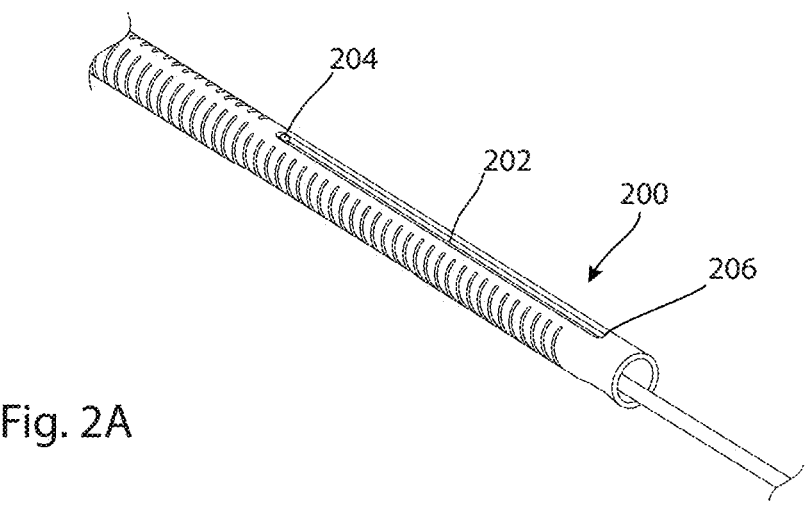
FIGS. 2A and 2B illustrate perspective and section views, respectively, of a locking mechanism on an adjustable medical device, according to embodiments of the present disclosure.
Figure 2B:
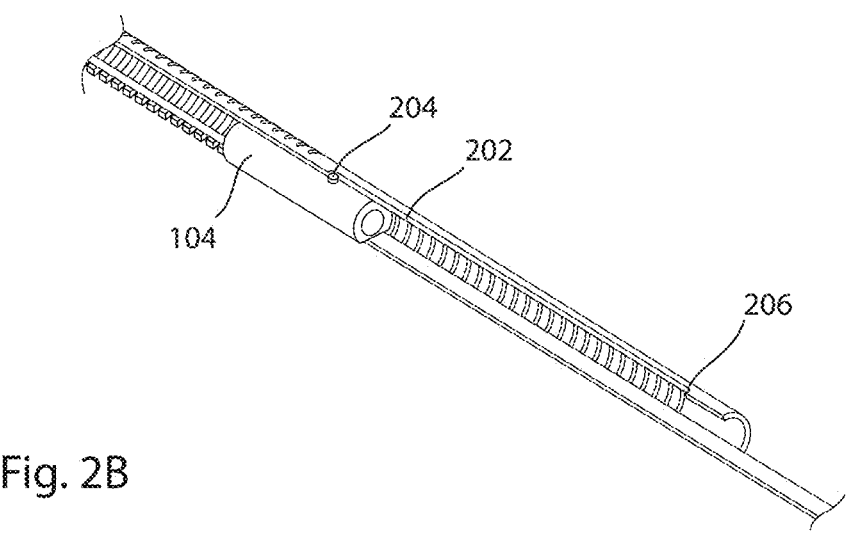

The device 100 can comprise a locking mechanism to lock the shuttle 104 in a proximally pulled position. FIGS. 2A and 2B show an embodiment of a locking mechanism 200. FIG. 2A shows an external view of the device 100. FIG. 2B shows a cut-away view of the device 100, showing the shuttle 104 within the device 100. The locking mechanism 200 may comprise a track 202. A pin 204 may be attached to the shuttle 104 and configured to slide along the track 202. The track 202 may lead to a slot or opening 206 having a distal wall against which the pin 204 can rest, thereby preventing the pin 204 from moving distally and locking the shuttle 104 into position. Other locking mechanisms 200 are also possible. For example, the shuttle 104 can be locked into position using a flexible screw running on the upper side of the shuttle 104. The screw can be configured to be screwed into an anchor portion of the device 100 (e.g., plug 112). Turning the screw can cause the shuttle 104 to move towards or away from the anchor. The screw can extend along the length of the spine portion 108. The screw may not extend out of the anchor when in the stiffened configuration as the spine 108 maintains its length between the collapsed and stiff configurations. In other embodiments, a screw and clip mechanism can be used.

Figures 3A, 3B:
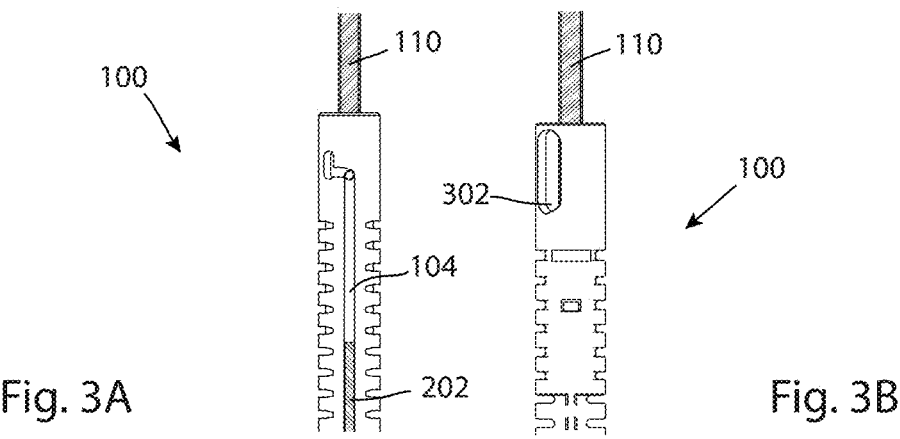
FIGS. 3A-3F show magnified side views of a locking and release mechanism on an adjustable medical device, according to embodiments of the present disclosure.
Figures 3C, 3D:
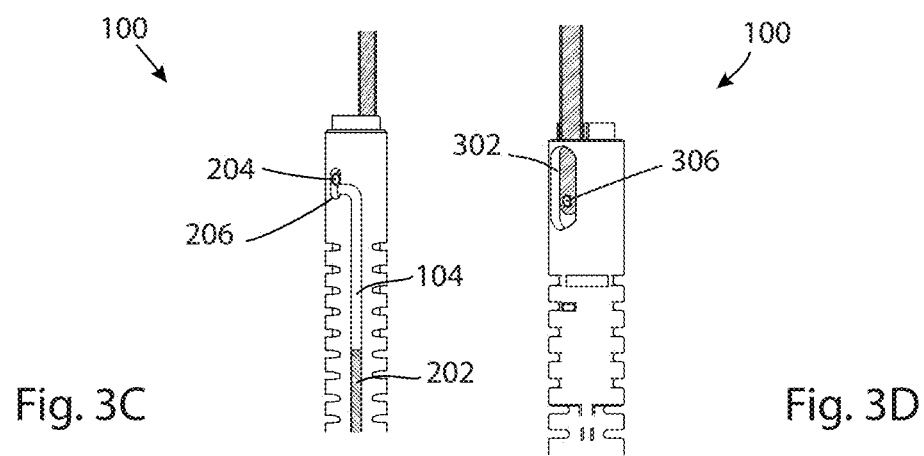
Figures 3E, 3F:
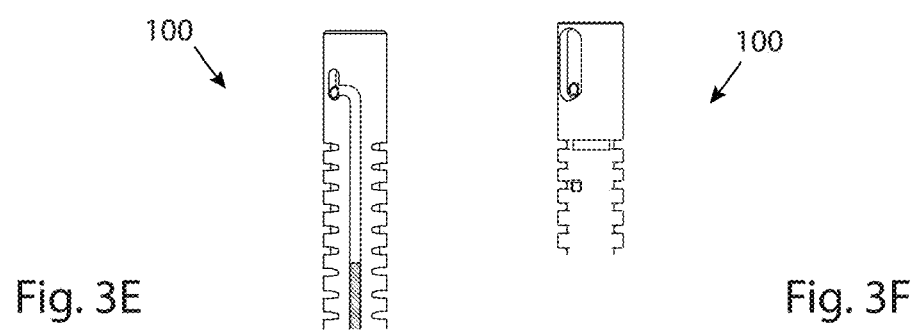

FIGS. 3A-3B illustrate a detailed view of a locking mechanism 300 like the locking mechanism 200, further comprising a disengagement feature configured to allow the pull member 110 to disengage from the shuttle 104 when the shuttle 104 is pulled into a locked position. FIGS. 3A and 3B illustrate the device 100 with the shuttle 104 pulled proximally along the track 202, but not yet placed into a locked position. FIG. 3A shows the track 202 and the locking opening 206. FIG. 3B shows a release window 302 positioned at a different portion of the device 100. As the pin 204 is moved into the locking opening 206, the shuttle 104 may twist, as shown in FIGS. 3C and 3D. The twisting of the shuttle 104 may position the connection between the shuttle 104 and the pull member 110 in the release window 302, shown in FIG. 3D. The connection may comprise an aperture 304 on the pull member 110 engaged with a pin 306 on the shuttle 104. Moving the aperture 304 engaged with the pin 306 to the release window 302 may cause the pull member 110 to disengage from the shuttle 104. FIGS. 3E and 3F show the device 100 after the pull member 110 has been disengaged and withdrawn.

Various factors can influence the radius of curvature of the device 100 in the locked or stiffened configuration 100b. For example, the configuration of the spine 108 can influence the configuration of the locked curvature. A spine portion 108 that coils around the device 100 can produce a locked device with a helical configuration. The coil angle and pitch of the spine portion 108 can determine the shape of the stiffened device as described herein.

Figure 4A:
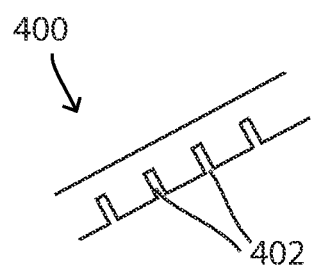
FIGS. 4A-5D show schematics of various embodiments of shape changing features for adjustable medical devices, according to embodiments of the present disclosure.
Figure 4B:
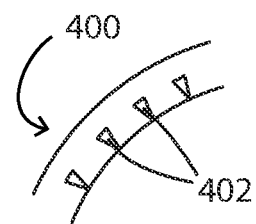
Figure 4C:
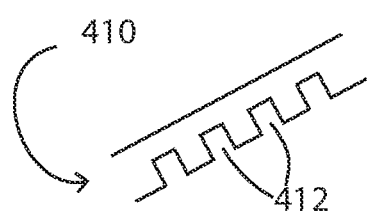
Figure 4D:
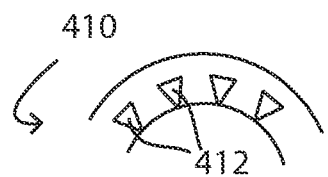

As noted above, the radius of curvature can be dependent on a total width of the openings. For example, FIGS. 4A and 4B show a device 400 with narrower openings 402 than those openings 412 shown in the device 410 of FIGS. 4C and 4D. The device 410 with the wider openings 412 has a deeper curve (smaller radius of curvature) (FIG. 4D) that that of the device 400 with the smaller openings 402 (FIG. 4B).

Figure 5A:
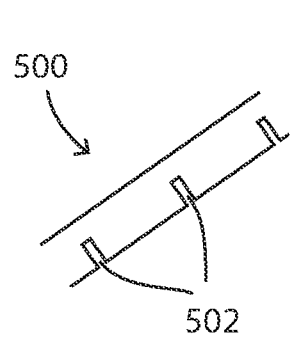
Figure 5B:
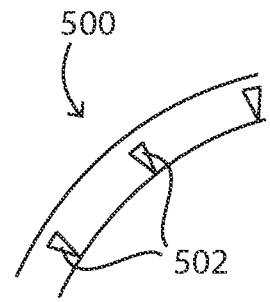
Figure 5C:
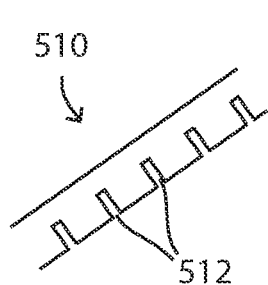
Figure 5D:
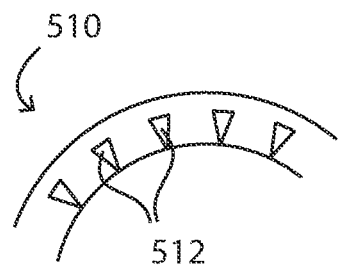

The density of the openings or the frequency of the openings along the length of the device can also determine a radius of curvature of the device, as a device with a higher density of openings has a higher total width of the openings. FIGS. 5A and 5B show a device 500 with fewer openings 502 than the device 510 of FIGS. 5C and 5D. The device 510 with a higher density of openings 512 has a higher radius of curvature (FIG. 5D) than that of the device 500 with the less dense openings 502 (FIG. 5B).

It will be understood by one of ordinary skill in the art that any of the devices described herein (e.g., 100, 140, 400, 410, 500, 510) may comprise any number, shape, or density of openings (e.g., 102, 142, 402, 412, 502, 512) as desired.

Figure 6:
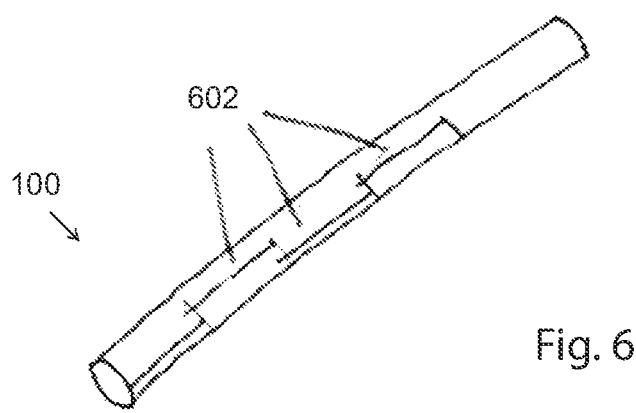
FIG. 6 illustrates a perspective view of another adjustable medical device, according to embodiments of the present disclosure.

In some embodiments, the device 100 may comprise multiple locking mechanisms 602 along a length of the device 100 as shown in FIG. 6. In such a device 100, multiple shuttles, tension members, and locking mechanisms can be used to separately and/or independently stiffen and lock various bending portions of the device 100. Each bending portion may comprise a proximal anchor portion comprising a locking mechanism (e.g., similar to locking portion 206 of FIGS. 2A-2B) that can be placed into contact with the corresponding shuttle to cause the corresponding bending portion to curve. In some embodiments, such a configuration can be used to sequentially lock portions of the device 100 and/or to achieve more complex stiffened configurations. For example, as the device 100 is deployed from a delivery catheter, the deployed portions can be stiffened and locked. This sequential locking can be performed manually by a clinician or, alternatively, can be performed by an automated system (e.g., a delivery system). In some embodiments, the act of exposing the device 100 or the relative motion between the delivery catheter and the device 100 can cause the exposed portions to be curved and locked. In some embodiments, a portion of the device 100 can comprise a first shape for delivery and a second, different shape when deployed. For example, a tip of the device 100 can be curved during delivery to aid with navigation. The device 100 can be stiffened into a different shape when deployed. In some embodiments, multiple shuttles are used with the different locking mechanisms. In other embodiments, one shuttle can be locked into different positions, causing different portions of the device 100 to be curved. Allowing this sort of sequential stiffening of the device 100 can allow the device 100 to form the path it takes after exiting the delivery catheter, which can diminish the need for a guide wire or guide catheter.

Figure 7A:
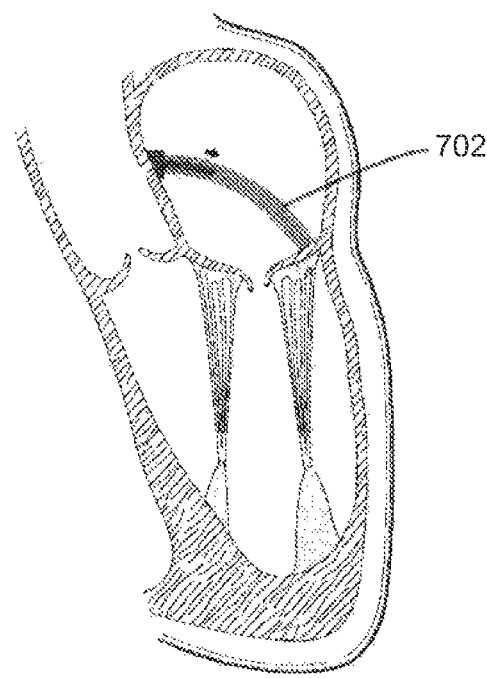
FIGS. 7A-7E are section views of the left side of the heart illustrating a method of deploying an adjustable medical device at the mitral valve, according to embodiments of the present disclosure.
Figure 7B:
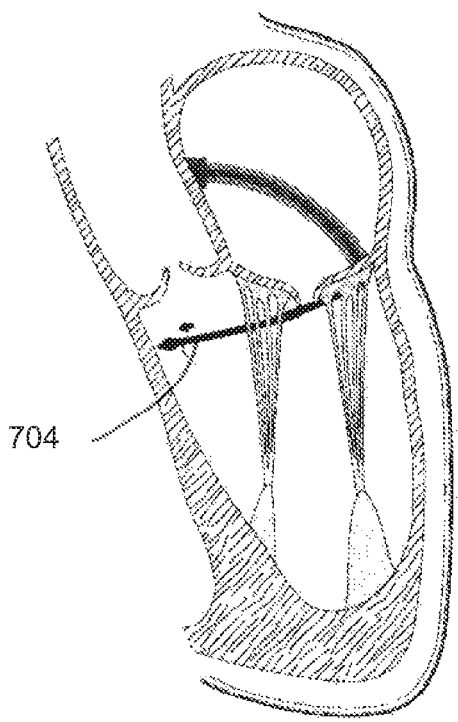
Figure 7C:
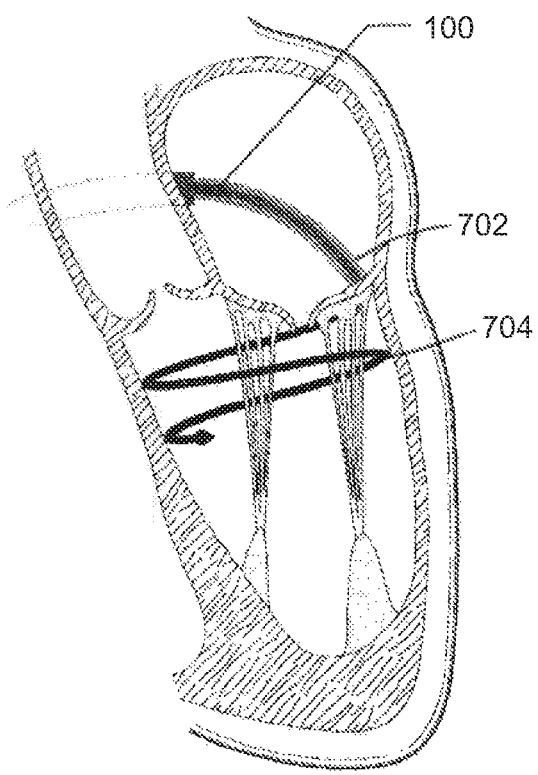
Figure 7D:
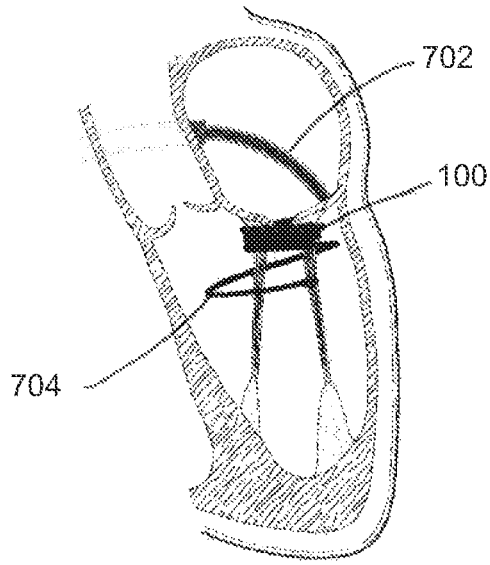
Figure 7E:
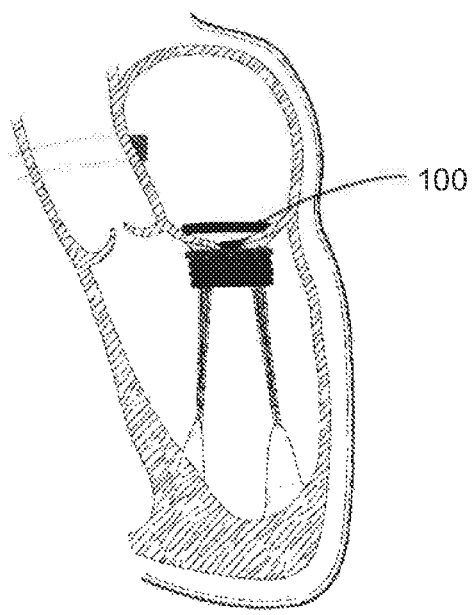

In some embodiments, the device 100 can be used as a dock for anchoring a valve prosthesis during a mitral valve repair or replacement procedure, as shown in FIGS. 7A-7E. FIG. 7A illustrates delivery catheter 702 positioned through the atrial septum after transseptal puncture. A guidewire 704 may be inserted into the heart via the delivery catheter 702 and through tissue at or near the anteromedial commissure, as shown in FIG. 7B. The guidewire 704 may be advanced such that it coils around the chordae tendineae in the left ventricle, as shown in FIGS. 7B and 7C. The device 100, or any of the devices described herein, may then be advanced through the catheter 702 and over the guidewire 704, as shown in FIG. 7D. The device 100 can be inserted in a slackened configuration 100a. The shape of the device 100 may mimic the guidewire 704 during delivery to the chordae tendineae. Once the device 100 is deployed around the chordae tendineae, it can be locked into the stiffened configuration 100b, as shown in FIG. 7E. As shown, the device 100 may form a helical shape in the stiffened configuration 100b with at least one coil around the chordae tendineae in the left ventricle and one coil in the left atrium. In some embodiments, the entire device 100 may be located in the left ventricle, with no coils sitting in the left atrium after deployment. The guidewire 704 can be retracted once the device 100 is in place. In some embodiments, the device 100 may comprise multiple bending portions as described above with respect to FIG. 6. Retracting the guidewire 704 from the device 100 can be coordinated with locking the device 100 so that the device 100 is locked into shape from its distal end towards its proximal end as the distal tip of the guidewire 704 moves from the distal end towards the proximal end of the device 100 as it is retracted. A valve prosthesis (not shown) may be delivered to the mitral valve and anchored to the mitral valve with the device 100 after the device 100 is deployed as described in U.S. patent application Ser. Nos. 16/594,946 and 16/546,901, and U.S. Provisional Application Nos. 62/720,853, 62/742,043, 62/755,996, 62/784,280, 62/813,963, 62/815,791, 62/820,570, 62/828,835, 62/833,425, 62/833,430 62/851,245, 62/872,016, 62/873,454, 62/879,979, and 62/894,565, previously incorporated herein by reference for all purposes.

Figure 8A:
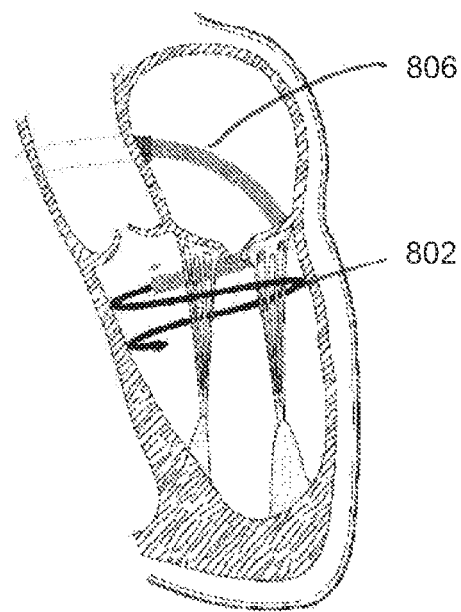
FIGS. 8A-8D are section views of the left side of the heart illustrating another embodiment of a method of deploying a, adjustable medical device at the mitral valve, according to embodiments of the present disclosure.
Figure 8B:
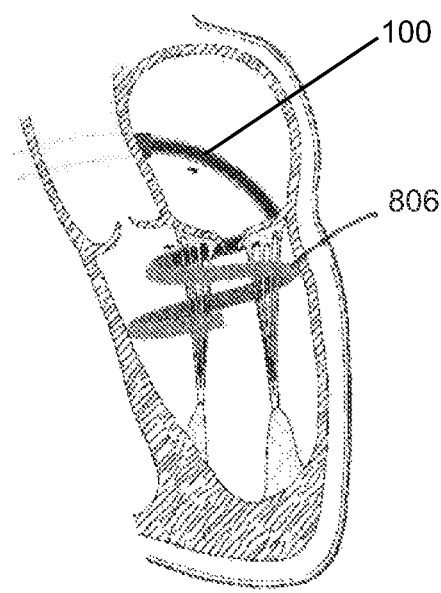
Figure 8C:
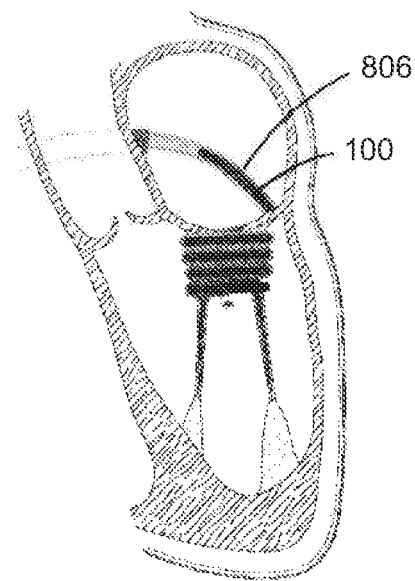
Figure 8D:
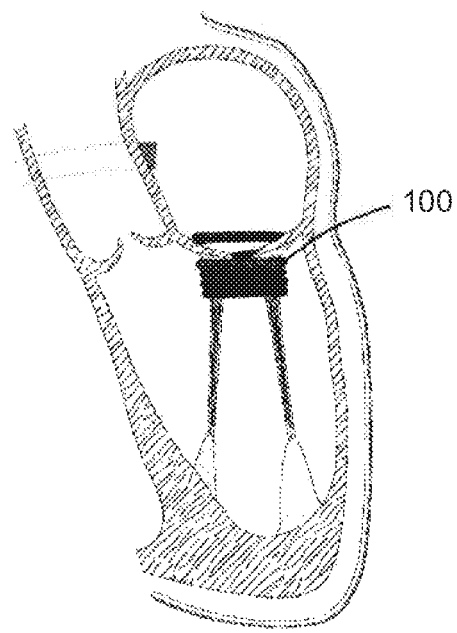

FIGS. 8A-8D illustrate a similar method to that shown in FIGS. 7A-7E; however, in the method of FIGS. 8A-8D, the device 100 is deployed through a guide catheter 806 instead of over a guidewire 802. FIG. 8A shows the delivery catheter 806 positioned through the atrial septum after transseptal puncture. A guidewire 802 may then be inserted through tissue at or near the anteromedial commissure and advanced such that it coils around the chordae tendineae in the left ventricle, as shown in FIG. 8A. The guide catheter 806 may be advanced over the guidewire 802, as shown in FIG. 8B. The guidewire 802 may then be withdrawn. The device 100 may then be advanced through the guide catheter 806, as shown in FIG. 8B. The guide catheter 806 may then be withdrawn, as shown in FIG. 8C. As shown in FIG. 7E, the device 100 may form a helical shape in the stiffened configuration with at least one coil around the chordae tendineae in the left ventricle and one coil in the left atrium. In some embodiments, the entire device 100 may be located in the left ventricle, with no coils sitting in the left atrium after deployment. The guide catheter 806 can be retracted once the device 100 is in place. In some embodiments, the device 100 may comprise multiple bending portions as described above with respect to FIG. 6. Retracting the guide catheter 806 from the device 100 can be coordinated with locking the device 100 so that the device 100 is locked into shape from its distal end towards its proximal end as the distal tip of the guide catheter 806 moves from the distal end towards the proximal end of the device 100 as it is retracted. A valve prosthesis (not shown) may be delivered to the mitral valve and anchored to the mitral valve with the device 100 after the device 100 is deployed as described in U.S. patent application Ser. Nos. 16/594,946 and 16/546,901, and U.S. Provisional Application Nos. 62/720,853, 62/742,043, 62/755,996, 62/784,280, 62/813,963, 62/815,791, 62/820,570, 62/828,835, 62/833,425, 62/833,430 62/851,245, 62/872,016, 62/873,454, 62/879,979, and 62/894,565, previously incorporated herein by reference for all purposes.

It will be appreciated that the device 100 can be used in other configurations as well. For example, in some embodiments, the device 100 can be used for non-occlusive ablation. The device 100 can be advanced to an area to be treated in a slackened or relaxed configuration. Once the device 100 reaches the target area, the device 100 can be locked into a stiffened configuration. In some embodiments, the device 100 can be moved into the stiffened configuration without actually locking it into place. Instead, it can be held in the stiffened configuration during ablation, and then released to move the device 100 to another ablation site or to withdraw the device 100. The stiffened configuration can comprise a predetermined curve configured to put the device 100 into contact with an area to be ablated. For example, the device 100 can be configured to coil around a perimeter of a blood vessel. The shape of the curve can be selected to ensure good contact between the device 100 and the area to be ablated. The spine portion 108 can be the outer most portion of the device 100 when in the stiffened configuration. The device 100 can comprise at least one electrode (e.g., 1, 2, 3, 4, 5, 6, 7, 8, or more electrodes) located such that they can be positioned against an area to be ablated in the stiffened configuration. In some embodiments, at least a portion of the device 100 itself (e.g., the spine portion 108) can comprise a metal and serve as the electrode. In some embodiments, in which the device 100 is used for non-occlusive ablation, the device 100 comprises a lumen through which blood can flow.

In some embodiments, the device 100 can be used in an anchor for an embolic protection device such as a filter for use during a cardiac intervention procedure. The device 100 can advantageously be delivered in a small profile and then deployed to a larger desired shape. The devices described herein can have certain advantages over shape memory devices that are able to be delivered in a slack configuration and then assume a deployed shape upon delivery. The devices described herein can comprise greater stiffness and strength in the deployed position than shape memory devices in a deployed position. Shape memory devices having deployed configurations with a much greater diameter than the delivered configuration (e.g., a coil) must be delivered in a catheter strong enough to maintain the shape memory device in a straight configuration during delivery as the shape memory device will bias towards the larger diameter configuration. The devices of the current application are not biased during delivery and do not need to be held in place during delivery by a stronger or thicker catheter.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A medical device, comprising:
    an elongate body having a first configuration and a second configuration, the second configuration having a different shape from the first configuration;
    a plurality of openings on the elongate body configured to allow the elongate body to change shape from the first configuration to the second configuration;
    a shuttle axially moveable within the elongate body;
    a tension member extending distally from the shuttle and connecting the shuttle to a distal portion of the elongate body;
    a pull member extending proximally from the shuttle, wherein pulling the shuttle proximally along the elongate body with the pull member causes the elongate body to transition from the first configuration to the second configuration; and
    a locking mechanism configured to hold the shuttle in a proximally pulled position to lock the elongate body in the second configuration.

2. The medical device of claim 1, wherein the elongate body is flexible in the first configuration and rigid in the second configuration.

3. The medical device of claim 1, wherein the elongate body is configured to be connected to an end of a catheter.

4. The medical device of claim 1, wherein the plurality of openings extend from a spine portion of the elongate body.

5. The medical device of claim 4, wherein the spine portion curves around at least a portion of the elongate body.

6. The medical device of claim 4, wherein a width of the openings changes between the first configuration and the second configuration.

7. The medical device of claim 1, wherein the locking mechanism comprises a pin attached to the shuttle that is positioned in and configured to slide along a track extending along a length of the elongate body.

8. The medical device of claim 1, wherein the elongate body further comprises a release window configured to allow disengagement of the pull member from the shuttle.

9. The medical device of claim 1, wherein the locking mechanism is disposed within the elongate body.

10. The medical device of claim 1, wherein the tension member is configured to elongate when the shuttle moves proximally away from the distal portion.

11. A method of advancing a medical device towards a target area, comprising:
    advancing an elongate body towards the target area and out of a distal end of a delivery catheter;
    manipulating a pull wire to move a shuttle axially within the elongate body to a first position to lock the elongate body into a first curved shape;
    manipulating the pull wire to move the shuttle axially into a second position to lock the elongate body into a second curved shape at or near the target area, the second curved shape different from the first curved shape.

12. The method of claim 11, wherein the second position is different from the first position.

13. The method of claim 11, wherein the first curved shape comprises a curve along a first portion of the elongate body, and wherein the second curved shape comprises a curve over a second portion of the elongate body, the second portion different from the first portion.

14. The method of claim 13, wherein the second portion is larger than and encompasses the first portion.

15. The method of claim 13, wherein the first curved shape comprises a curve at a tip of the elongate body.

16. The method of claim 11, wherein the target area comprises a native valve in a heart.

17. The method of claim 16, further comprising advancing the elongate body from a first side of the native valve to a second side of the native valve.

18. The method of claim 16, further comprising, after moving the medical device into the second curved shape, expanding at least a portion of an expandable valve prosthesis adjacent the native valve.

19. The method of claim 11, wherein the elongate body comprises a plurality of openings extending from a spine portion of a wall of the device.

20. The method of claim 11, wherein the first curved shape is defined by a length of a tension member connecting the shuttle to a distal portion of the elongate member.

21. The method of claim 20, wherein the length of the tension member is longer when the elongate member assumes the second curved shape.

22. A method of delivering a valve prosthesis anchor to a native valve, comprising:
- advancing an elongate body in a flexible delivery configuration towards the native valve and out of a distal end of a delivery catheter;
- manipulating a pull wire to move a shuttle axially along the elongate body to cause the elongate body to transition from the flexible delivery configuration to a rigid helical configuration such that the elongate body forms at least one coil around chordae of the native valve; and
- locking a position of the shuttle within the elongate body to lock the elongate body in the rigid helical configuration around the chordae.

* * * * *